United States Patent
Goodman et al.

(10) Patent No.: US 11,484,479 B2
(45) Date of Patent: Nov. 1, 2022

(54) FORMULATION FOR THE ELIMINATION OF CARIOGENIC AND OPPORTUNISTIC PATHOGENS WITHIN THE ORAL CAVITY

(71) Applicant: Research Institute at Nationwide Children's Hospital, Columbus, OH (US)

(72) Inventors: Steven David Goodman, Hilliard, OH (US); Lauren Mashburn Warren, Gahanna, OH (US)

(73) Assignee: Research Institute at Nationwide Children's Hospital, Columbus, OH (US)

(*) Notice: Subject to any disclaimer, the term of this patent is extended or adjusted under 35 U.S.C. 154(b) by 0 days.

(21) Appl. No.: 16/437,921

(22) Filed: Jun. 11, 2019

(65) Prior Publication Data

US 2019/0388309 A1    Dec. 26, 2019

Related U.S. Application Data

(63) Continuation of application No. 15/744,725, filed as application No. PCT/US2016/042153 on Jul. 13, 2016, now abandoned.

(60) Provisional application No. 62/192,470, filed on Jul. 14, 2015.

(51) Int. Cl.
| | |
|---|---|
| *A61K 8/11* | (2006.01) |
| *A61Q 11/00* | (2006.01) |
| *A61K 8/73* | (2006.01) |
| *A61Q 17/00* | (2006.01) |
| *A61K 9/50* | (2006.01) |

(52) U.S. Cl.
CPC .............. *A61K 8/11* (2013.01); *A61K 8/73* (2013.01); *A61K 9/5036* (2013.01); *A61Q 11/00* (2013.01); *A61Q 17/005* (2013.01); *A61K 2800/412* (2013.01); *A61K 2800/56* (2013.01)

(58) Field of Classification Search
None
See application file for complete search history.

(56) References Cited

U.S. PATENT DOCUMENTS

| | | | |
|---|---|---|---|
| 5,549,908 A * | 8/1996 | Smith ................. | A61L 15/28 424/444 |
| 7,811,591 B2 | 10/2010 | Bakaletz et al. | |
| 8,329,187 B2 | 12/2012 | Lazzari et al. | |

(Continued)

FOREIGN PATENT DOCUMENTS

| | | |
|---|---|---|
| JP | 2012-527898 A | 11/2012 |
| JP | 5670783 B2 | 2/2015 |

(Continued)

OTHER PUBLICATIONS

Desiderio et al. ("Intraphagocytic Killing of *Salmonella typhimurium* by Liposome-Encapsulated Cephalothin", The Journal of Infectious Diseases, vol. 148, No. 3 (Sep. 1983), pp. 563-570) (Year: 1983).*

(Continued)

*Primary Examiner* — Robert A Wax
*Assistant Examiner* — Quanglong N Truong
(74) *Attorney, Agent, or Firm* — Foley & Lardner LLP

(57) ABSTRACT

Provided herein are microspheres containing an antimicrobial agent encapsulated within a glycosidic polymer and use thereof, especially to inhibit the growth of carie-causing organism.

13 Claims, 12 Drawing Sheets

(56) References Cited

U.S. PATENT DOCUMENTS

| | | | |
|---|---|---|---|
| 8,933,029 | B2 | 1/2015 | McNicol et al. |
| 9,017,656 | B2 | 4/2015 | Hancock et al. |
| 9,155,792 | B2 | 10/2015 | Cottarel et al. |
| 9,603,878 | B2 | 3/2017 | Berry et al. |
| 9,687,449 | B2 | 6/2017 | Harel |
| 9,745,366 | B2 | 8/2017 | Goodman et al. |
| 10,369,176 | B2 | 8/2019 | Goodman et al. |
| 10,624,934 | B2 | 4/2020 | Goodman et al. |
| 10,642,934 | B2 | 5/2020 | Heck et al. |
| 2003/0229065 | A1 | 12/2003 | Levy et al. |
| 2005/0112235 | A1 | 5/2005 | Shefer et al. |
| 2005/0221439 | A1 | 10/2005 | Bakaletz et al. |
| 2005/0266069 | A1 | 12/2005 | Simmons et al. |
| 2007/0207210 | A1 | 9/2007 | Brown et al. |
| 2007/0286822 | A1 | 12/2007 | Sanders et al. |
| 2010/0303723 | A1 | 12/2010 | Farokhzad et al. |
| 2011/0008493 | A1 | 1/2011 | Zorea |
| 2011/0027328 | A1 | 2/2011 | Baig et al. |
| 2011/0236306 | A1 | 9/2011 | Goodman et al. |
| 2012/0148615 | A1 | 6/2012 | Masignani et al. |
| 2012/0189558 | A1 | 7/2012 | Prendergast |
| 2013/0183323 | A1 | 7/2013 | Wang |
| 2014/0363410 | A1 | 12/2014 | Degonda et al. |
| 2014/0377192 | A1 | 12/2014 | Schaeffer-Korbylo et al. |
| 2015/0010654 | A1 | 1/2015 | Arnold et al. |
| 2015/0086542 | A1 | 3/2015 | Goodman et al. |
| 2015/0342848 | A1 | 12/2015 | Bhushan et al. |
| 2016/0120915 | A1 | 5/2016 | Blaser et al. |
| 2016/0228476 | A1 | 8/2016 | Cutcliffe et al. |
| 2017/0182205 | A1 | 6/2017 | Zupancic et al. |
| 2017/0209504 | A1 | 7/2017 | Goodman et al. |
| 2017/0215417 | A1 | 8/2017 | Bhushan et al. |
| 2018/0207067 | A1 | 7/2018 | Goodman et al. |
| 2018/0303900 | A1 | 10/2018 | Bakaletz et al. |
| 2019/0000971 | A1 | 1/2019 | Bakaletz et al. |
| 2019/0388309 | A1 | 12/2019 | Goodman et al. |
| 2020/0155620 | A1 | 5/2020 | Goodman et al. |
| 2021/0100854 | A1 | 4/2021 | Goodman et al. |
| 2021/0290701 | A1 | 9/2021 | Besner et al. |

FOREIGN PATENT DOCUMENTS

| | | |
|---|---|---|
| WO | WO-98/50018 A1 | 11/1998 |
| WO | WO-02/085295 A2 | 10/2002 |
| WO | WO-2006/017816 A2 | 2/2006 |
| WO | WO-2009/006699 A1 | 1/2009 |
| WO | WO-2010/138522 A2 | 12/2010 |
| WO | WO-2012/034090 A1 | 3/2012 |
| WO | WO-2014/016417 A1 | 1/2014 |
| WO | WO 2014/121304 A1 | 8/2014 |
| WO | WO-2015/038339 A1 | 3/2015 |
| WO | WO-2015/134808 A2 | 9/2015 |
| WO | WO-2016/066763 A1 | 5/2016 |
| WO | WO 2020/028871 A1 | 2/2020 |

OTHER PUBLICATIONS

A.-L Cornaz Gudet et al., "Simple method of in vitro diffusion of nicotine across procine palatine mucosa", European Journal of Pharmaceutics and Biopharmaceutics, vol. 43, No. 3, Jun. 1, 1997, pp. 259-264.

Catia Ornelas-Megiatto et al., "Aerosolized Antimicrobial Agents Based on Degradable Dextran Nanoparticles Loaded with Silver Carbene Complexes", Molecular Pharmaceutics, vol. 9, No. 11, Oct. 19, 20102, pp. 3012-3022.

Extended European Search Report issued in EP 16825137.9 dated Feb. 14, 2019, 9 pages.

Final Office Action on U.S. Appl. No. 15/744,725 dated Dec. 17, 2018.

International Preliminary Report on Patentability issued in PCT Application No. PCT/US2016/042153 dated Jan. 25, 2018, 8 pages.
International Search Report and Written Opinion (ISA/US) for PCT Patent Application No. PCT/US2016/042153, dated Sep. 27, 2016.

Jaleh Varshosaz, "The promise of chitosan microspheres in drug delivery systems", Expert Opinion on Drug Delivery, vol. 4, No. 3, May 9, 2007. pp. 263-273.

Nowakowski, "Antimicrobial activity of nicotine against a spectrum of bacterial and fungal pathogens", J. Med. Microbiol., vol. 49., Dec. 31, 2000, pp. 674-675.

U.S. Office Action on U.S. Appl. No. 15/744,725 dated May 17, 2018.

Allaker et al., "Non-conventional therapeutics for oral infections," Virulence, vol. 6, No. 3, Apr. 2015, pp. 196-207.

Beer et al., "Poly (lactic-glycolic) acid copolymer encapsulation of recombinant adenovirus reduces immunogenicity in vivo," Gene Therapy, vol. 5, Jan. 5, 1998, pp. 740-746.

Chavarri et al., "Microencapsulation of a probiotic and prebiotic in alginate-chitosan capsules improves survival in simulated gastro-intestinal conditions," International Journal of Food Microbiology, vol. 142, Jun. 22, 2010, pp. 185-189.

Chen et al., "The effect of immobilization of probiotic Lactobacillus reuteri DPC16 in sub-100 μm microcapsule on food-borne pathogens", World J. Microbial. Biotechnol., vol. 28, No. 6, Mar. 30, 2012, pp. 2447-2452.

Cook et al., "Microencapsulation of a synbiotic into PLGA/alginate multiparticulate gels," International Jounral of Pharmaceutics, vol. 466, Mar. 20, 2014, pp. 400-408.

Cook et al., "Microencapsulation of probiotics for gastrointestinal delivery," Journal of Controlled Release, vol. 162, Jun. 11, 2012, pp. 56-67.

Crittenden et al., "Synbiotic Microcapsules That Enhance Microbial Viability during Nonrefrigerated Storage and Gastrointestinal Transit", Applied and Environmental Microbiology, vol. 72, No. 3, Mar. 2006, 2280-2282.

Kadajji et al., "Water Soluble Polymers for Pharmaceutical Applications," Polymers, vol. 3, Nov. 11, 2011, pp. 1972-2009.

Kumari et al., "Biodegradable polymeric nanoparticles based drug delivery systems," Colloids and Surfaces B: Biointerfaces, vol. 75, Sep. 8, 2009, pp. 1-18.

Petreska Ivanovska et al., "Comparative evaluation of viability of encapsulated Lactobacillus casei using two different methods of microencapsulation," International Journal of Pharmaceutical and Phytopharmacological Research, vol. 4, No. 1, pp. 20-24 (Abstract only).

Pliszczak et al., "Improvement of an encapsulation process for the preparation of pro- and prebiotics-loaded bioadhesive microparticles by using experimental design," European Journal of Pharmaceutical Sciences, vol. 44, Jun. 25, 2011, pp. 83-92.

Salas-Jara et al., "Biofilm forming Lactobacillus: New challenges for the development of Probiotics". Microorganisms, vol. 4, No. 35, Sep. 20, 2016, 14 pages.

Sathyabama et al., "Co-encapsulation of probiotics with prebiotics on alginate matrix and its effect on viability in simulated gastric environment," LWT—Food Science and Technology, vol. 57, Dec. 16, 2013, pp. 419-425.

Sultana et al., "Encapsulation of probiotic bacteria with alginate-starch and evaluation of survival in simulated gastrointestinal conditions and in yoghurt," International Journal of Food Microbiology, vol. 62, May 26, 2000, pp. 47-55.

Thurnheer et al., "Colonisation of gingival epithelia by subgingival biofilms in vitro: role of 'red complex' bacteria," Archives in Oral Biology, vol. 59, No. 9, Sep. 2014, pp. 1-24.

Wu et al., "Preparation of sodium fluoride-loaded gelatin microspheres, characterization and cariostatic studies," J Microencapsul., vol. 21, No. 8, Dec. 2004, pp. 889-903, Abstract Only.

Albandar, "Epidemiology and risk factors of periodontal diseases", Dental clinics of North America, vol. 49, No. 3, Jun. 28, 2005, pp. 517-532.

Darveau RP. The oral microbial consortium's interaction with the periodontal innate defense system. DNA and cell biology. 2009;28(8):389-95. Epub May 14, 2009. doi:10.1089/dna.2009. 0864. PubMed PMID: 19435427; PMCID: 2883565.

Darveau, "Periodontitis: a polymicrobial disruption of host homeostasis", Nature reviews Microbiology, vol. 8, No. 7, Jul. 2010, pp. 481-490.

(56) References Cited

OTHER PUBLICATIONS

Dzink et al., "The predominant cultivable microbiota of active and inactive lesions of destructive periodontal diseases", Journal of clinical periodontology, vol. 15, No. 5, Sep. 8, 1987, pp. 316-323.
Eke PI, Dye BA, Wei L, Thornton-Evans GO, Genco RJ, Cdc Periodontal Disease Surveillance workgroup: James Beck GDRP. Prevalence of periodontitis in adults in the United States: 2009 and 2010. Journal of dental research.2012;91(10):914-20. Epub Sep. 1, 2012. doi: 10.1177/0022034512457373. PubMed PMID: 22935673.
Estrela et al., "Combining Biofilm-Controlling Compounds and Antibiotics as a Promising New Way to Control Biofilm Infections," Pharmaceuticals, vol. 3, May 11, 2010, pp. 1374-1393.
Grossi et al., "Assessment of risk for periodontal disease. I. Risk indicators for attachment loss", Journal of periodontology, vol. 65, No. 3, Sep. 15, 1993, pp. 260-267.
Hajishengallis G, Liang S, Payne MA, Hashim A, Jotwani R, Eskan MA, McIntosh ML, Alsam A, Kirkwood KL, Lambris JD, Darveau RP, Curtis MA. Low-abundance biofilm species orchestrates inflammatory periodontal disease through the commensal microbiota and complement. Cell host & microbe.2011;10(5):497-506. Epub Nov. 1, 2011.
John, A-K. et al. (2011) "Reversible Daptomycin Tolerance of Adherent *Staphylococci* in an Implant Infection Model," Antimicrobial Agents and Chemotherapy 55(7):3510-3516.
Joo, H-S. et al. (2012) "Molecular Basis of In Vivo Formation by Bacterial Pathogens," Chemistry & Biology 19:1503-1513.
Kadajji et al., "Water Soluble Polymers for Pharmaceutical Applications", Polymers, vol. 3, No. 4, Nov. 11, 2011, pp. 1972-2009.
Kirketerp-Moller et al., "Distribution, Organization, and Ecology of Bacteria in Chronic Wounds," Journal of Clinical Microbiology, vol. 46, No. 8, Aug. 2008, pp. 2717-2722.
Lamont RJ, Jenkinson HF. Life below the gum line: pathogenic mechanisms of Porphyromonas gingivalis. Microbiology and molecular biology reviews: MMBR.1998;62(4):1244-63. Epub Dec. 5, 1998. PubMed PMID: 9841671; PMCID: 98945.
Maeda et al., "Oral streptococcal glyceraldehyde-3-phosphate dehydrogenase mediates interaction with Porphyromonas gingivalis fimbriae", Microbes and infection / Institut Pasteur., vol. 6, No. 13, Sep. 11, 2004, pp. 1163-1170.
Nakagawa et al., "Clinical, microbiological and immunological studies on recurrent periodontal disease", Journal of clinical periodontology, Jul. 31, 1989, vol. 17, No. 7 Pt 1, pp. 426-434.
Nowakowska, J. et al. (2014) "Foreign Body Infection Models to Study Host-Pathogen Response and Antimicrobial Tolerance of Bacterial Biofilm," Antibiotics 3:378-397, Aug. 2014.
Petersen PE, Ogawa H. Strengthening the prevention of periodontal disease: the WHO approach. Journal of periodontology. 2005;76(12):2187-93. Epub Dec. 8, 2005. doi: 10.1902/jop.2005. 76.12.2187. PubMed PMID: 16332229.
Priyadarshini R, Cugini C, Arndt A, Chen T, Tjokro NO, Goodman SD, Davey ME, The nucleoid-associated protein HUß affects global gene expression in Porphyromonas gingivalis. Microbiology. 2013; 159(Pt2):219-29.First Published: Feb. 1, 2013.
Reffuveille et al., "A Broad-Spectrum Antibiofilm Peptide Enhances Antibiotic Action against Bacterial Biofilms", Antimicrobial Agents and Chemotherapy, vol. 58, No. 9, Sep. 2014, pp. 5363-5371.
Slots J, Gibbons RJ. Attachment of *Bacteroides melaninogenicus* subsp. *asaccharolyticus* to oral surfaces and its possible role in colonization of the mouth and of periodontal pockets. Infection and immunity.1978;19(1):254-64. Epub Jan. 1, 1978. PubMed PMID: 24002; PMCID: 414075.
Thurnheer et al., "Colonisation of gingival epithelia by subgingival biofilms in vitro: role of 'red complex' bacteria", Arch Oral Biol., vol. 59, No. 9, Sep. 2014, pp. 1-24.
Tjokro NO, Rocco CJ, Priyadarshini R, Davey ME, Goodman SD. A biochemical analysis of the interaction of Porphyromonas gingivalis HU PG0121 protein with DNA. PloS one. 2014;9(3):e93266. Epub Apr. 1, 2014 . doi: 10.1371.
Wu et al., "Preparation of sodium fluoride-loaded gelatin microspheres, characterization and cariostatic studies", J. Microencapsul., vol. 21, No. 8, Dec. 2004, Abstract, 1 page.
Fei Wu, et al., "Development of dextran nanoparticles for stabilizing delicate proteins", Nanoscale Research Letters, 2013, 8:197, pp. 1-8.
US Final Office Action dated Jun. 15, 2022, from U.S. Appl. No. 16/820,463.
US Notice of Allowance dated Jun. 30, 2022, from U.S. Appl. No. 16/820,463.
US Notice of Allowance dated May 11, 2022, from U.S. Appl. No. 16/449,320.

* cited by examiner

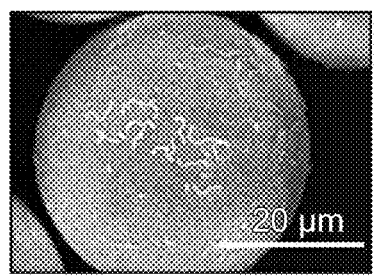 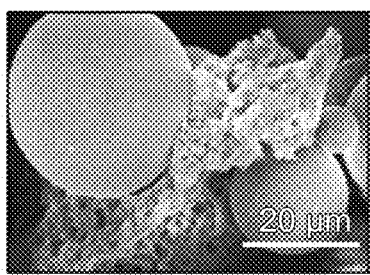
FIG. 5A          FIG. 5B
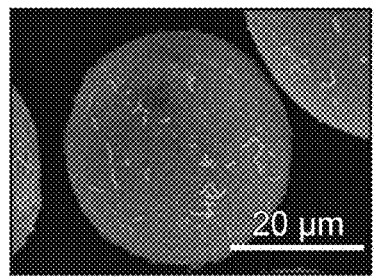 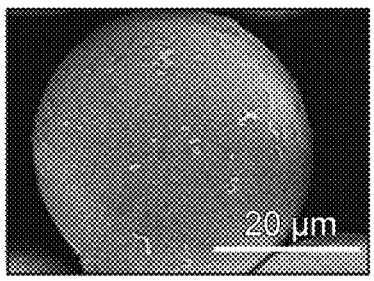
FIG. 5C          FIG. 5D
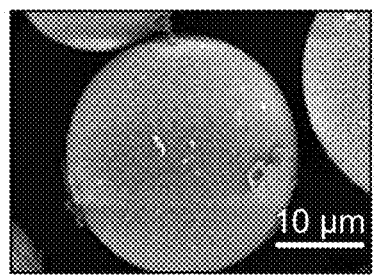 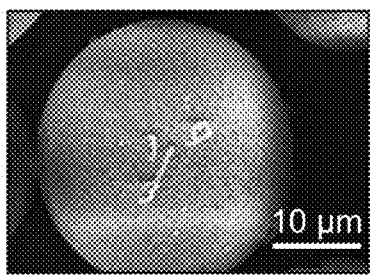
FIG. 5E          FIG. 5F
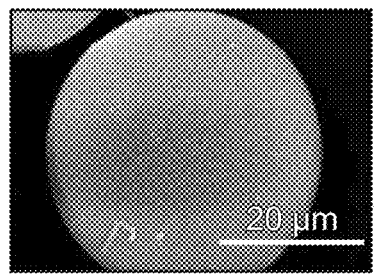 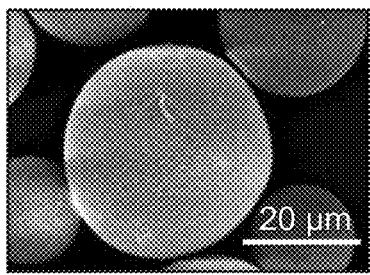
FIG. 5G          FIG. 5H
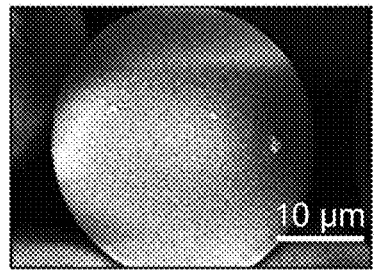 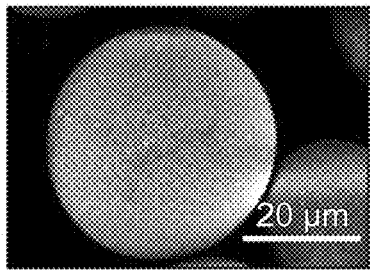
FIG. 5I          FIG. 5J

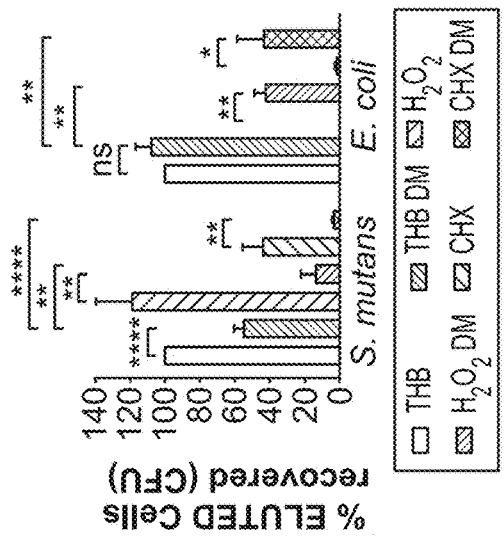
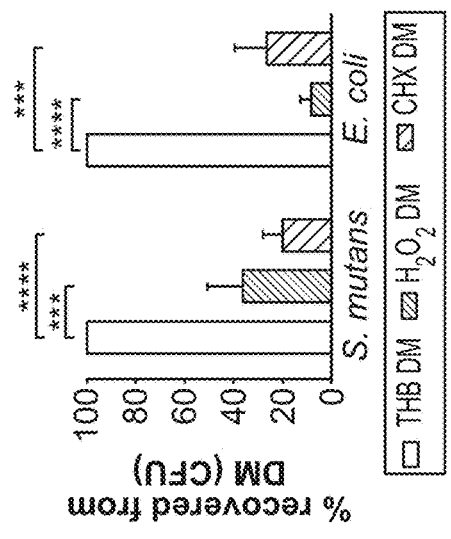
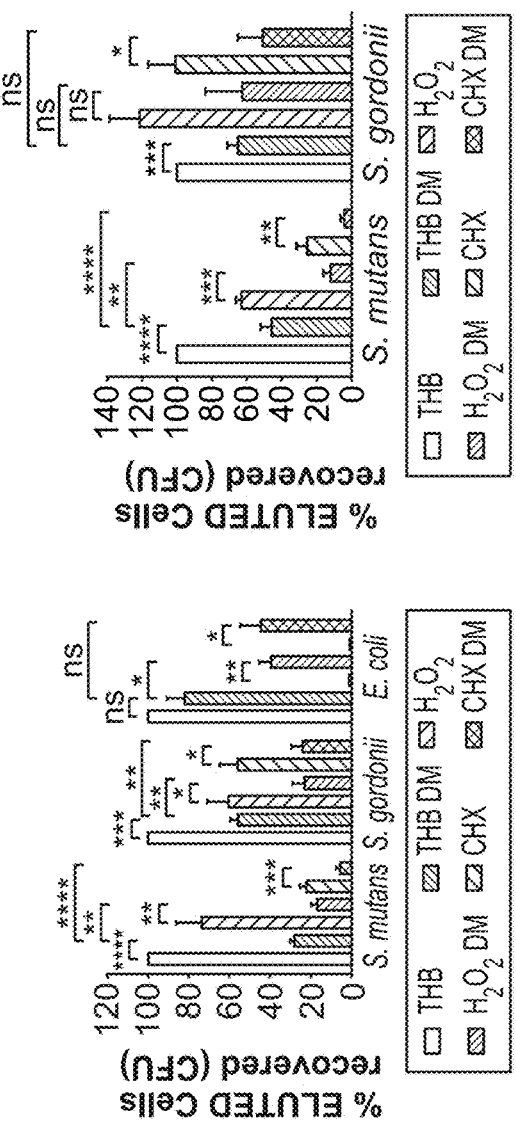
FIG. 12A
FIG. 12B

FORMULATION FOR THE ELIMINATION OF CARIOGENIC AND OPPORTUNISTIC PATHOGENS WITHIN THE ORAL CAVITY

CROSS-REFERENCE TO RELATED APPLICATION

This application is a continuation application of U.S. application Ser. No. 15/744,725, filed Jan. 12, 2018, which claims priority under 35 U.S.C. § 371 of International Application No. PCT/US2016/042153, filed Jul. 13, 2016, which in turn claims priority under 35 U.S.C. § 119(e) to U.S. Provisional Application No. 62/192,470, filed Jul. 14, 2015, the content of each of is incorporated herein by reference in its entirety.

BACKGROUND

Dental caries is a transmissible infectious disease that occurs in 84% of adults with one or more natural teeth, and is caused by the demineralization of the tooth surface by bacteria residing in the oral cavity (Kassebaum, N. J. et al. (2015) J Dental Res., Vol. 94(5):650-658). According to the 2000 Surgeon General's report on oral health care in America, 78% of 17 year olds have at least one decayed tooth or filling (United States. Public Health Service, Office of the Surgeon General, National Institute of Dental and Craniofacial Research (2000) Oral Health in America: A Report of the Surgeon General). The Surgeon General reports that the cost of oral health care alone was responsible for 4.7% of the nation's health expenditures in 1998, approximately $53.8 billion (United States. Public Health Service, Office of the Surgeon General, National Institute of Dental and Craniofacial Research (2000) Oral Health in America: A Report of the Surgeon General). Understandably, researchers are continually investigating possible new avenues for the prevention of tooth decay.

The standard methods for the prevention of tooth decay are mechanical debridement, (brushing the teeth for two minutes twice daily and flossing at least once a day), regular dental checkups and limiting dietary intake of sugars. Additional methods of prevention include dental sealants, fluoride, chlorhexidine, salivary enhancers and antimicrobial agents. However, most are general approaches for the prevention of tooth decay with no available methods specific for the bacteria that are responsible for dental caries without significantly affecting the healthy commensal flora, i.e., available treatments to date disrupt all the flora in the oral cavity.

Dental plaque accumulates on the tooth surface and is comprised of a large and diverse population of microbes representing over 700 bacterial species of which only 50% are able to be cultivated (Aas, J. A. et al. (2005) J. Clin. Microbiol 43:5721-5732; Filoche, S. et al. (2010) J Dent Res 89:8-18); most of these are commensal bacteria making up the 'healthy plaque' (Aas, J. A. et al. (2005) J. Clin. Microbiol 43:5721-5732). However, among these oral bacteria, *Streptococcus mutans* has been shown to be a major contributor to dental caries, where a correlation has been established between the presence of *S. mutans* in patients with caries and the absence of *S. mutans* in patients that lack dental caries (Loesche, W. J. (1986) Oral Microbiol Immunol 1:65-70). In addition, the amount of *S. mutans* present in the mouth has been shown to correlate with the individual's dietary intake of table sugar (sucrose) (Ashley, F. P. et al. (1997) Arch. Oral Biol 22:409-414; Cury, J. A. et al. (2001) Braz. Dent J. 12:101-104; Petti, S. et al. (1996) New Microbiol. 19:133-140). Moreover, *S. mutans* and other oral Streptococci including *Streptococcus oralis*, *Streptococcus sanguis*, and *Streptococcus gordonii* are opportunistic pathogens and have been associated with causing infective endocarditis (IE) (Nomura, R. et al. (2006) J Med Microbiol 55:1135-1140; Nomura, R. et al. (2014) Infection and Immunity 82:5223-5234). IE is caused by bacteria entering the bloodstream followed by bacterial colonization on the heart lining, heart valves, and/or blood vessels. While uncommon, IE can be initiated by dental procedures and routine dental care such as brushing and flossing (Sonbol, H. et al. (2009) Oral Microbiol Immunol 24:177-182). Thus there is a demand for new therapeutic approaches that target oral streptococci that are drivers of pathogenesis including dental caries and opportunistic infections.

Existing treatments for the prevention of tooth decay involve flooding the oral cavity with oral health care products, thereby disrupting both healthy (commensal) and pathogenic (harmful) bacteria. Thus, a need exists for a targeted treatment for the elimination of cariogenic and potentially harmful (opportunistic) bacteria with minimal disturbance of commensals. This disclosure satisfies this need and provides related advantages as well.

SUMMARY

This disclosure provides a microsphere that comprises or alternatively consists essentially of, or yet further consists of, an antimicrobial agent encapsulated within a polymer having a glycosidic bond, e.g. a glycosidic polymer-based microsphere, e.g., an insoluble cross-linked dextran. In one aspect, any glycosidic polymer having an alpha-1,6 linkage, an alpha-1,3 linkage, or any combinations thereof can be used in the microsphere. In one aspect, the glycosidic polymer-based microsphere comprises, or consists essentially of, or yet further consists of, an insoluble cross-linked dextran, e.g., the commercially available dextranomer or Sephadex (GE Healthcare, Pistcataway, N.J.) or a mimetic thereof or combination thereof.

Any suitable antimicrobial can be encapsulated within the microsphere, non-limiting examples of such include without limitation those that are active against organisms that cause dental caries and associated disease, e.g., one or more from the group of hydrogen peroxide, chlorhexidine, penicillin, streptomycin, erythromycin, xylitol, fluoride, triclosan, alcohol, and cetylpyridinium chloride.

The microspheres can be combined with a carrier, e.g., a pharmaceutically acceptable carrier. The composition can be formulated as a solid, a semi-solid or a liquid and can optionally comprise, or alternatively consist essentially of, or yet further consist of, one or more of a flavoring agent or a color agent. The compositions can be formulated as a lyophilized powder, a tablet, a chewable tablet, a suspension, a lozenge, a dissolvable lozenge, a gum, a gel, a toothpaste, a fluoride rinse, or a mouthwash. The compositions comprise a plurality of the microspheres, the plurality of the microspheres having the same or different diameter and/or the same or different antimicrobial agent. The compositions can be formulated as a solid, a semi-solid, or a liquid.

The microspheres and compositions comprising, or alternatively consisting essentially of, or yet further consisting of, the microspheres can be used in oral formulations to inhibit or selectively inhibit the growth of, and/or selectively remove carie-causing organisms from the oral cavity, by administering to the oral cavity of the subject an effective amount of the microsphere or formulation containing it. Non-limiting examples of carie-causing organisms include without limitation, *S. mutans*, *S. gordonii*, *S. sobrinus*, *S. oralis*, *S. sanguis*, *S. mitis*, *S. salivarius*, and *S. cristatus*.

The microspheres and compositions also are useful in methods for treating and/or preventing infective endocarditis (IE) in a subject by treating the bacteria in the oral cavity that may result in endocarditis. The method comprises, or alternatively consists essentially of, or yet further consists of, administering to the oral cavity of the subject in need thereof, an effective amount of the microsphere or compositions described herein, thereby treating and/or preventing infective endocarditis.

The amount of microsphere to be administered to the subject will vary with the subject, the time from ingestion of food or other carie-promoting substance, and the carie-promoting organism to be treated. Non-limiting examples of such include of about 5 to about 250 mg of microsphere per dose, or alternatively from about 15 to about 250 mg; or alternatively from about 25 to 100 mg; or alternatively from about 25 to about 75 mg; or about 25 to about 50 mg, or microsphere per dose. Multiple doses can be administered as needed, e.g., at least twice, at least thrice, or at least four times a day as needed. The volume of liquid (pre-lyophilization or processing of the loaded microsphere) is from about 1 mg/microliter of liquid carrier to about 5 mg/μl of liquid carrier, or from about 1.5 to about 2.5 mg/μl of liquid carrier, or alternatively of about 2 mg/μl of liquid carrier (all pre-lyophilization or further processing.

Also provided herein is a kit comprising, or alternatively consisting essentially of, or yet further consisting of, a microsphere or composition containing the microsphere and instructions for use in the methods as disclosed herein.

BRIEF DESCRIPTION OF THE DRAWINGS

(FIG. 1A) *S. mutans* grown in THB or THB+3% sucrose to early log phase was incubated for 5 min. without and with 125 μl of DM (G-25 superfine, G-10, G-15, G-25 fine, or G-25 medium, ordered from smallest to largest diameter respectively) on a microspin column. (FIGS. 1B & 1C) *S. mutans* UA159 was grown in THB (FIG. 1B) or THB+3% sucrose (FIG. 1C) to early log phase ($OD_{650nm}$ ~0.3) or late log phase ($OD_{650nm}$ ~0.8) followed by incubation for <10 sec., 1, and 5 min. without and with 125 μl G-25 superfine DM. Following centrifugation at 100×g for 1 min., the $OD_{650nm}$ of the eluate for each culture was measured. The percentage of cells adhered to DM was calculated for each size compared to the absence of DM (set at 0%). Error bars represent the standard error mean (SEM). Asterisks indicate the statistical significance of assays performed with DM vs. no DM ($P<0.002$; *$P<0.005$; ****$P<0.0001$; ns: not significant).

(FIG. 2A) Wild type strains of *S. mutans* were grown to early log phase ($OD_{650nm}$ ~0.3) in THB or THB+3% sucrose then incubated without and with 125 μl (12.5 mg) G-25 superfine DM. (FIG. 2B) *S. mutans* UA159 and GS-5 wild type and gtfBCD mutant strains were grown to early log phase ($OD_{650nm}$ ~0.3) in the presence and absence of 3% sucrose and incubated for 5 min. without and with 125 μl (12.5 mg) G-25 superfine DM. The percentage of cells bound to the DM resin was calculated for each strain compared to without DM (set at 0%) for the same strain. Error bars represent the standard error mean (SEM). Asterisks indicate the statistical significance of assays performed with DM vs. no DM or as designated with bars (*$P<0.05$; $P<0.001$; *$P<0.005$; ****$P<0.0001$; ns: not significant).

(FIG. 4A) Serial dilutions of the DM in suspension were plated onto THB agar to determine the amount of *S. mutans* removed from the peg. (FIG. 4B) The agarose-DM mixtures was removed and placed in 200 μl THB and incubated at 37° C. for 5 min. to melt the agarose. The mixture was then serially diluted and plated onto THB agar to determine the amount of *S. mutans* removed from the peg. (FIGS. 4A & 4B) Pegs were detached from the lid and sonicated for 5 min. in 200 μl THB followed by serial dilutions and plating on THB agar to determine the amount of *S. mutans* remaining on the peg. The percentage of cells remaining and removed from the peg was compared in the absence and presence of DM. Error bars represent the standard error mean (SEM). Asterisks indicate the statistical significance between assays as designated by bars (*$P<0.005$; **$P<0.0001$).

FIGS. 5A-5J show scanning electron microscopy of bacteria bound to DM. Bacterial cells were grown to early log phase ($OD_{650nm}$ ~0.3) and were then incubated without and with 125 μl (12.5 mg) G-25 superfine DM. *S. mutans* wild type (FIGS. 5A & 5B); *S. mutans* ΔgtfBCD (FIGS. 5C & 5D); *S. gordonii* (FIGS. 5E & 5F); *S. cristatus* (FIGS. 5G & 5H); *E. coli* (FIGS. 5I & 5J). Bacterial cells were grown in the absence (FIGS. 5A, 5C, 5E, 5G, & 5I) and presence of sucrose (FIGS. 5B, 5D, 5F, 5H, & 5J). The bacteria/DM mixture was fixed in glutaraldehyde overnight followed by staining with osmium tetroxide and then dehydrated with a stepwise gradient of ethanol and hexamethyldisilazane and dried overnight. The bacteria/DM mixture was mounted on 15 mm stubs with double sided carbon tape and sputter coated with palladium/gold. Samples were imaged using a Hitachi S-4800 Field Emission Scanning Electron Microscope.

(FIG. 10A) S. mutans UA159 was grown in THB to early log phase ($OD_{650nm}$ ~0.3) followed by incubation with increasing amounts of G-25 superfine DM (0-25 mg) for 5 min. (FIG. 10B) S. mutans UA159 was grown in THB to early log phase ($OD_{650nm}$-0.3) followed by the addition of 3% sucrose. Immediately (<10 sec.), 10, 20, and 30 min. after sucrose exposure, S. mutans was incubated without and with 125 µl (12.5 mg) G-25 superfine DM. The percentage of cells adhered to DM was calculated for each time point compared to without DM (set at 0%) for the same length of time. Error bars represent the standard error mean (SEM). Asterisks indicate the statistical significance of assays performed with DM vs. no DM or as designated by bars (P<0.008; *P<0.001; ****P<0.0001; ns: not significant).

FIGS. 12A-12D show cells adhered to DM are eliminated by the presence of toxic cargo. (left panels) S. mutans ($10^6$ CFUs) (MW30; Erm$^R$; (Desai, K. et al. (2012) Journal of Bacteriology 194:3774-3780)), S. gordonii ($10^8$ CFUs) and E. coli ($10^8$ CFUs) were grown to early log phase without (FIGS. 12A & 12B) or with (FIGS. 12C & 12D) 3% sucrose as monocultures and exposed to DM containing media (THB), 1.5% hydrogen peroxide ($H_2O_2$) or 0.2% chlorhexidine (CHX) within the DM lumen or exposed to the same volume of toxic cargo without DM for 1 min. (middle panels) S. mutans ($10^6$ CFUs) (MW30; Erm$^R$; (Desai, K. et al. (2012) Journal of Bacteriology 194:3774-3780)) and S. gordonii ($10^8$ CFUs) or (right panels) S. mutans ($10^6$ CFUs) (Erm$^R$; (Desai, K. et al. (2012) Journal of Bacteriology 194:3774-3780)) and E. coli ($10^8$ CFUs) were mixed just prior to incubation with toxic cargo or toxic cargo contained within the DM lumen for 1 min. (FIGS. 12A & 12C) Eluted cells and the (FIGS. 12B & 12D) DM/bacteria slurry that remained after centrifugation were plated to determine the amount of recovered cells that did not adhere to DM and those cells that did bind DM respectively. The percentage of cells recovered when incubated with media (set at 100%) was compared to the amount recovered that was incubated with toxic cargo. Error bars represent the standard error mean (SEM). Asterisks indicate the statistical significance as designated by bars (*P<0.05; P<0.005; *P<0.001; ****P<0.0001; ns: not significant).

DETAILED DESCRIPTION

Definitions

Figure 1A:
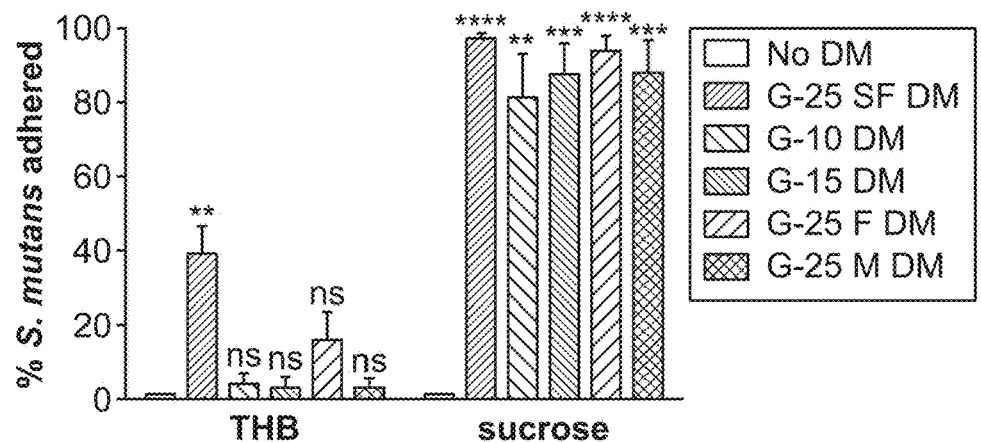
FIGS. 1A-1C show various sizes and exposure times of DM tested for the removal of *S. mutans*.

All technical and patent publications cited herein are incorporated herein by reference in their entirety. Throughout this disclosure, some citations are referenced by an Arabic numeral, the complete citation of which is provided at the end of the specification. All references are incorporated by reference herein to more fully describe the state of the art to which this disclosure pertains.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise.

"Comprising" refers to compounds, compositions and methods including the recited elements, but not excluding others. "Consisting essentially of," when used to define compounds, compositions or methods, shall mean excluding other elements that would materially affect the basic and novel characteristics of the claimed technology. "Consisting of," shall mean excluding any element, step, or ingredient not specified in the claim. Embodiments defined by each of these transition terms are within the scope of this disclosure.

As used herein, "microsphere" refers to a microscopic particle less than about 1000 μm in diameter (wet bead size). In some embodiments, the particles range in size from about 1 μm μm to about 1,000 μm in diameter, or alternatively between about 10 μm to about 500 μm, or alternatively between about 10 μm to about 500 μm, or alternatively between about 10 μm to about 800 μm, or alternatively between about 10 μm to about 700 μm, or alternatively between about 10 μm to about 600 μm, or alternatively between about 20 μm to about 1000, or alternatively between about 20 μm to about 800 μm, or alternatively between about 20 μm to about 700 μm, or alternatively between about 20 μm to about 600 μm, or alternatively between about 20 μm to about 500 μm; or alternatively between about 30 μm to about 1000 μm, or alternatively between about 30 μm to about 900 μm, or alternatively between about 30 μm to about 800 μm, or alternatively between about 30 μm to about 700 μm, or alternatively between about 100 μm to about 900 μm, or alternatively between about 200 μm to about 1000 μm, or alternatively between about 40 μm to about 1000 μm, or alternatively between about 40 μm to about 500 μm, or alternatively between about 40 μm to about 400 μm; or alternatively between about 40 μm to about 300 μm; or alternatively between about 40 μm to about 200 μm, or alternatively from about 40 μm to about 150 μm, or alternatively from about 40 μm to about 120 μm, or alternatively between about 20 μm to about 300 μm, or alternatively between about 20 μm to about 200 μm or alternatively between about 20 μm to about 150 μm or alternatively between about 20 μm to about 140 μm or alternatively less than about 500 μm, or alternatively less than about 400 μm, or alternatively less than about 300 μm, or alternatively less than about 250 μm, or alternatively less than about 200 μm, alternatively lets than about 150 μm, or alternatively less than about 100 μm, or alternatively less than about 75 μm, or alternatively less than about 50 μm. In a further aspect, the average diameter of the microsphere is from about 10 μm to about 40 μm (dry) or about 17 μm to 70 μm (wet).

As used herein, "polymer" refers to a naturally-occurring, synthetic or semi-synthetic large molecule (macromolecule) typically composed of repeating structural units connected by covalent chemical bonds. Polymers useful for the implementation of this disclosure have molecular weights in the range of 1 to 5000 kDa. The polymers can be stable, degradable and made of random copolymers or block copolymers.

As used herein, a "glycosidic polymer" intends a polymer with at least one glycosidic bond.

As used herein, the term "carrier" encompasses any of the standard carriers, such as a phosphate buffered saline solution, buffers, water, and emulsions, such as an oil/water or water/oil emulsion, and various types of wetting agents. The carrier also can include stabilizers and preservatives. In one aspect of the invention, the carrier is a buffered solution such as, but not limited to, phosphate buffered saline solution, a gel, or another pharmaceutically acceptable carrier.

As used herein, "antimicrobial" refers to a compound, mixture of compounds, or biologic agent that can provide a beneficial effect when administered to a patient.

As used herein, "pharmaceutical agent", "pharmaceutically-active agent", and "pharmaceutically-active compound" refer to a compound, mixture of compounds, or biologic agent, such as an antibody or fragment thereof, that can provide a beneficial effect through a pharmacological mode of action when administered to a patient.

As used herein, the terms "treat," "treating," and "treatment" refer to a method of alleviating or abrogating a disease and/or its attendant symptoms. The effect may be prophylactic in terms of completely or partially preventing a disorder or sign or symptom thereof, and/or may be therapeutic in terms of a partial or complete cure for a disorder and/or adverse effect attributable to the disorder.

As used herein, "administer," "administering" or "administration" refers to the delivery of a microsphere or composition to a patient in a manner suitable for the treatment of a particular disease or condition or to inhibit the growth of and/or selectively remove carie-causing organisms. "Administration" can be effected in one dose, continuously or intermittently throughout the course of treatment. Methods of determining the most effective means and dosage of administration are known to those of skill in the art and will vary with the composition used for therapy, the purpose of the therapy, the condition being treated, and the subject being treated. Single or multiple administrations can be carried out with the formulation or dose level and pattern being selected by the treating physician. Suitable dosage formulations and/or routes of administration are known in the art and will vary with the formulation used for treatment, the purpose of the treatment, the health condition or disease stage of the subject being treated and target cell or tissue. Non-limiting examples of route of administration include oral administration, vaginal, rectal, nasal administration, injection, and topical application.

A "patient" or a "subject" refers to any higher organism that is susceptible to disease. Examples of such higher organisms include, without limitation, mice, rats, rabbits, dogs, cats, horses, cows, pigs, sheep, fish and reptiles. In some embodiments, "patient" or "subject" refers to a human being.

As used herein, the term "an effective amount" refers to that amount of the microspheres or composition as described herein, which has the effect of (a) preventing a disorder from occurring in a subject that may be predisposed to a disorder, but may have not yet been diagnosed as having it; (b) inhibiting a disorder, i.e., arresting its development; or (c) relieving or ameliorating the disorder or the symptoms of the disorder.

Antimicrobial-Containing Microspheres

Disclosed herein are microspheres comprising an antimicrobial agent encapsulated within a glycosidic polymer-based microsphere. In one aspect, the microsphere is comprised of a glycosidic polymer-based microsphere, such as an insoluble cross-linked dextran. A non-limiting example of such includes commercially available insoluble cross-linked dextran marketed under the trade name Sephadex (dextranomer) or a mimetics thereof. Sephadex (SEparation PHArmacia DEXtran, cross-linked dextran of varying sizes) is a macroscopic bead of cross-linked dextran (one type of glucan). Varieties of Sephadex are commercially available and differ by their size (fine, medium, course, super fine (G01, G-15, G025 superfine, G-25 fine and G-25 medium) and degree of cross-linking, providing an extensive fractionation range. G-10 has a fractionation range of less than or equal to 700; G-15 has a fractionation range of less or equal to than 1500; G-15 has a fractionation range of less or equal to than 1500; G-25 has a fractionation range of about 1,000 to about 5,000; G-15 has a fractionation range of less or equal to than 1500; G-25 has a fractionation range of less or equal to than 1500; G-50 has a fractionation range of about 1500 to about 30,000; less or equal to than 1500; G-75 has a fractionation range of about 3,000 to about 80,000; G-100 has a fractionation range of about 4,000 to about 150,000; G-150 has a fractionation range of about 5000 to about 300,000; and G-200 has a fractionation range of about 5,000 about 600,000.

As used herein, the term Sephadex mimetic intends any structure, for example a polymer structure that resembles Sephadex, e.g., a dextranomer or other polysaccharide consisting of glucose made into microspheres.

The average diameter of the microsphere can vary, for example having less than about 1000 μm in diameter (wet bead size). In some embodiments, the particles range in size from about 1 μm μm to about 1,000 μm in diameter, or alternatively between about 10 μm to about 500 μm, or alternatively between about 10 μm to about 500 μm, or alternatively between about 10 μm to about 800 μm, or alternatively between about 10 μm to about 700 μm, or alternatively between about 10 μm to about 600 μm, or alternatively between about 20 μm to about 1000, or alternatively between about 20 μm to about 800 μm, or alternatively between about 20 μm to about 700 μm, or alternatively between about 20 μm to about 600 μm, or alternatively between about 20 μm to about 500 μm; or alternatively between about 30 μm to about 1000 μm, or alternatively between about 30 μm to about 900 μm, or alternatively between about 30 μm to about 800 μm, or alternatively between about 30 μm to about 700 μm, or alternatively between about 100 μm to about 900 μm, or alternatively between about 200 μm to about 1000 μm, or alternatively between about 40 μm to about 1000 μm, or alternatively between about 40 μm to about 500 μm, or alternatively between about 40 μm to about 400 μm; or alternatively between about 40 μm to about 300 μm; or alternatively between about 10 μm to about 300 μm, or alternatively less than about 500 μm, or alternatively less than about 400 μm, or alternatively less than about 300 μm, or alternatively less than about 250 μm, or alternatively less than about 200 μm, alternatively lets than about 150 μm, or alternatively less than about 100 μm, or alternatively less than about 75 μm, or alternatively less than about 50 μm.

In another aspect, microsphere has a pre-selected surface area to mg of Sephadex used for the microsphere, e.g., from about $6\times10^7$ μm$^2$ to about $6\times10^8$ μm$^2$ per mg of Sephadex. In an another aspect, the microsphere comprises G25-superfine Sephadex and the microspheres have an average pre-selected surface area of from about $6\times10^7$ μm$^2$ to about $6\times10^8$ μm$^2$ per mg of Sephadex.

In a further aspect, the average diameter of the microsphere ranges from about 10 to about 40 μm (dry) (or about 17 to 70 μm (wet)) and the surface area to mg of Sephadex used for the microsphere is from about $6\times10^7$ μm$^2$ to about $6\times10^8$ μm$^2$ per mg of Sephadex. In a further aspect, the average diameter of the microsphere ranges from about 10 to about 40 μm (or about 17 to 70 μm (wet)) and the surface area to mg of Sephadex used for the microsphere is from about $6\times10^7$ μm$^2$ to about $6\times10^8$ μm$^2$ per mg of Sephadex, and the microsphere comprises G25-superfine Sephadex.

In another aspect, microsphere has a pre-selected surface area to mg of Sephadex used for the microsphere, e.g., from about $6\times10^7$ μm$^2$ to about $6\times10^8$ μm$^2$ per mg of Sephadex and contains about 2 mg of active agent per μl of liquid carrier in the microsphere (prior to processing). In an another aspect, the microsphere comprises G25-superfineSephadex and the microspheres have an average pre-selected surface area of from about $6\times10^7$ μm$^2$ to about $6\times10^8$ μm$^2$ per mg of Sephadex contains about 2 mg of active agent per μl of liquid carrier in the microsphere (prior to processing).

The antimicrobial agent is any agent that has activity against the target organism, non-limiting examples of such include hydrogen peroxide, chlorhexidine, penicillin, streptomycin, erythromycin, xylitol, fluoride, triclosan, alcohol, and cetylpyridinium chloride. The amount of the encapsulated agent will vary, e.g., from about 10 μl to about 250 μl, or from about 10 μl to about 200 μl, or from about 10 μl to about 150 μl, or from about 50 μl to about 250 μl, or from about 50 μl to about 150 μl, or from about 50 μl to about 250 μl, or from about 75 μl to about 250 μl.

Also provided herein is a composition comprising, or alternatively consisting essentially of, or yet further consisting of, a plurality of microspheres as described above. The microspheres in the composition can comprise microspheres having the same or different average diameter, and/or the same or different composition of microsphere, and/or the same or different antimicrobial agent.

The compositions can further comprise one or more of any of the standard carriers, such as a phosphate buffered saline solution, buffers, water, and emulsions, such as an oil/water or water/oil emulsion, and various types of wetting agents. The carrier also can include stabilizers, preservatives, a pharmaceutically acceptable flavoring agent, and a coloring agent. The microspheres and compositions containing them can be formulated as a solid, a semi-solid or a liquid, e.g., a chewable tablet, a dissolvable lozenge, a suspension, a gum, a gel, a toothpaste, a fluoride rinse, or a mouthwash.

Further provided are kits comprising one or more of the compositions, microspheres, or formulations as described herein and instructions for use.

Methods for Making the Microsphere Compositions

Also provided herein are methods for making the microspheres by combining an effective amount of the microsphere particle in the antimicrobial agent, e.g., Sephadex is mixed to hydration or wetting in an amount of the antimicrobial agent, e.g., hydrogen peroxide to produce a slurry. Excess antimicrobial is removed by any appropriate method, e.g., centrifugation, desiccation, and filtration, leaving the antimicrobial in the lumen of the micro sphere.

The microspheres can be combined with an appropriate carrier and formulated using methods known in the art. Additional agents such as buffers, stabilizers, preservatives, a pharmaceutically acceptable flavoring agent, or a coloring agent can be added. The microspheres and compositions containing them can be formulated as a solid, a semi-solid or a liquid, e.g., a tablet, a chewable tablet, a suspension, a lozenge, a dissolvable lozenge, a gum, a gel, a toothpaste, a fluoride rinse, or a mouthwash.

Therapeutic Methods

Also provided are methods for selectively inhibiting the growth of, and/or selectively removing carie-causing organisms from the oral cavity in a subject, by administering to the oral cavity of the subject an effective amount of the microsphere, composition or formulation as described herein, thereby inhibiting the growth of, and/or selectively removing carie-causing organisms from the oral cavity. While the examples provided herein are directed to the use in the oral cavity, this disclosure is not so limited and it is within the scope thereof that the compositions and formulations as provided herein can be administered in any appropriate manner to inhibit the growth of an organism any environment, e.g., topically or by suspension in a wound, for example, or in any appropriate environment, such as an industrial or residential setting. They can be used in the treatment of animals, e.g., sport animals or pets, or humans.

Also provided herein is a composition comprising, or alternatively consisting essentially of, or yet further consisting of, a plurality of microspheres as described above. The microspheres in the composition can comprise microspheres having the same or different average diameter, and/or the same or different composition of microsphere, and/or the same or different antimicrobial agent.

In one aspect, the microsphere, compositions and/or formulations are administered at least about 5 minutes, or alternatively at least about 7 minutes, or alternatively at least about 8 minutes, or at least about 10 minutes, or at least about 12 minutes, or alternatively at least about 15 minutes, or alternatively at least about 20 minutes, after the ingestion of or the presence of a food such as a high sugar food, by the subject. Mode of administration will vary with the formulation and can include dissolving a lozenge or alternatively swishing for an effective amount of time a mouthwash containing the microsphere.

Yet further provided is a method for treating and/or preventing infective endocarditis (IE), comprising administering to the oral cavity of the subject in need thereof, an effective amount of the microsphere, composition or formulation as described herein, thereby inhibiting the growth of, and/or selectively removing carie-causing organisms from the oral cavity. In one aspect, the microsphere, compositions and/or formulations are administered at least about 5 minutes, or alternatively at least about 7 minutes, or alternatively at least about 8 minutes, or at least about 10 minutes, or at least about 12 minutes, or alternatively at least about 15 minutes, or alternatively at least about 20 minutes, after the ingestion of or the presence of a food such as a high sugar food, by the subject. Mode of administration will vary with the formulation and can include dissolving a lozenge or alternatively swishing for an effective amount of time a mouthwash containing the micro sphere.

The selection of the microsphere, the antimicrobial and formulation will vary with the subject being treated and the target of the therapy. These are determined by a treating or recommending physician or dentist.

The amount of microsphere to be administered to the subject will vary with the subject, the time from ingestion of food or other carie-promoting food, and the carie-promoting organism to be treated. Non-limiting examples of such include of about 5 to about 250 mg of microsphere per dose, or alternatively from about 15 to about 250 mg; or alternatively from about 25 to 100 mg; or alternatively from about 25 to about 75 mg; or about 25 to about 50 mg, or microsphere per dose.

Kits Descriptive Embodiments Sephadex is cross-linked dextranomer microspheres (DM) typically used for gel filtration. In addition DM beads can be used for the affinity purification of glucosyltransferases (GTFs) from the caries causing bacterium *Streptococcus mutans*. Interestingly, Applicant demonstrates that whole cell cultures of planktonic and biofilm grown *S. mutans* adhered to hydroxy apatite coated pegs to mimic the tooth surface, specifically and readily attach to DM. Further investigation demonstrated that DM is a specific affinity resin for *S. mutans* and other cariogenic/pathogenic oral streptococci, whereas other commensal and probiotic strains fail to readily adhere to DM. Using antimicrobial cargo loaded into the DM lumen, Applicant demonstrates that when in co-culture with an oral commensal (modest binder) *S. mutans* was selectively killed over the commensal strain. In addition, a commensal strain that does not bind to DM was protected from the effects of the toxic cargo. This study introduces a novel means to safely and effectively reduce the pool of *S. mutans* and other oral pathogenic streptococci in the oral cavity with potentially limited disturbance of the necessary commensal (healthy) microbiota.

Although the aforementioned methods of preventing tooth decay have some practical value, here Applicant provides herein an alternative approach, which involves preferentially removing the caries-causing bacteria from amongst an otherwise healthy bacterial community by taking advantage of *S. mutans* capacity to bind glucan, a polymer of glucose. Launched by Pharmacia in 1959, Sephadex (SEparation PHArmacia DEXtran) is macroscopic beads of cross-linked dextran ($\alpha$ 1, 6 and $\alpha$ 1,3 linked glucose) or dextranomer microsphere (DM). These are the same types of glycosidic linkages found in mutan, the glucan synthesized by *S. mutans*. Varieties of DM are FDA approved and are commercially available. DM differ by their size (fine, medium, course, super fine) and degree of cross-linking effecting pore size and providing an extensive fractionation range. DM is typically used for size exclusion chromatography in the laboratory setting due to its relative inertness but interestingly, can be used as an affinity resin for the purification of *S. mutans* glucosyltransferases (GTFs) (Mooser, G. et al. (1985) Journal of Biological Chemistry 260:6907-6915). In fact the binding of GTFs to DM is virtually irreversible to the extent that guanidine hydrochloride is required to denature the GTFs to release them from this affinity resin (Mooser, G. et al. (1985) Journal of Biological Chemistry 260:6907-6915). Since these same GTFs are strongly associated with the cell wall of *S. mutans* (Kuramitsu, H. K. et al. (1978) Infection and immunity 20:652-659), Applicant investigated if *S. mutans* could specifically bind to DM. Applicant shows that *S. mutans* cells readily adhere to the DM resin, both in the form of planktonic cells and biofilms attached to a hydroxy apatite coated surface that mimic the natural state of *S. mutans* within the oral cavity. Other oral streptococci bound to DM with varying affinities where opportunistic pathogens displayed greater affinity for DM and the healthier commensal bacteria with less affinity. In fact, significantly more *S. mutans* was removed from a mixed culture with an oral commensal when treated with DM resin. Importantly, Applicant found that loading the lumen of the DM with antimicrobial cargo enables the elimination of bacterial cells that have preferentially adhered, whereas those that don't adhere were protected. In this study Applicant investigates the possibility of using DM-specific attachment as a method to specifically deplete *S. mutans* and other pathogenic streptococci from the oral cavity.

In one aspect, Applicant provides herein a new novel formulation using a dextranomer formulation suitable for pharmaceutical use, a resin commonly utilized in the laboratory setting for size exclusion chromatography (e.g., Sephadex). While similar products are also currently being used in humans for the treatment of wounds (Debrisan) and fetal incontinence (Solesta), to the best of Applicant's knowledge the cargo-carrying microsphere has not heretofore been used in an oral formulation for the targeted and specific attachment and removal of cariogenic and opportunistic bacteria from the oral cavity and thus preventing tooth decay and potentially infective endocarditis. Applicant is loading the lumen of the Sephadex with antimicrobial cargo that allows not only the cariogenic and pathogenic bacteria to bind, but also for them to also be eliminated.

In one aspect, Applicant's formulation is for the treatment of dental caries to be applied as a delivery system for removing specific cariogenic bacteria and potential harmful bacteria (opportunistic) from the oral cavity. This formulation could be used in oral health care as an additive in mouth wash, toothpaste, and/or chewing gum for the prevention of tooth decay. In addition this formulation could be utilized prior to dental services for the removal of opportunistic pathogens that could potentially cause infective endocarditis.

Applicant has devised a new treatment strategy for the prevention and treatment of tooth decay, by targeting and eliminating *mutans* streptococci (e.g., *Streptococcus mutans* and *Streptococcus sobrinus*), microorganisms that are major contributor of dental caries. This new approach also has the potential to target opportunistic pathogens associated with causing infective endocarditis (e.g., *S. mutans, Streptococcus gordonii, Streptococcus oralis*). To colonize the oral cavity, oral Streptococci utilize enzymes known as glucosyltransferases that convert sucrose (table sugar) to glucan (mutan/dextran polymers of glucose), a sticky carbohydrate that facilitates the attachment to the tooth surface. Dextranomer is a commercially available medium composed of cross-linked dextran spheres commonly used in the laboratory as a size exclusion resin. Dextranomer resins (e.g., Sephadex) has been used for purifying the glucosyltransferases of *S. mutans*, in fact once the glucosyltransferases bind to the resin, it is almost irreversible where guanidine hydrochloride (harsh chemical) is required for their removal. Because the glucosyltransferases are present on the surface of *S. mutans* (and other Streptococci) and exposed to the extracellular milieu Applicant use Sephadex to bind and sequester these bacteria (via the glucosyltransferases) present in the oral cavity.

There are 3 advantages to using Sephadex for the targeted removal of oral Streptococci. First, Sephadex provides a surface for binding, second Sephadex spheres contain a lumen for the storage of cargo, and third it is safe. Sephadex is supplied as a dry powder, therefore it can be hydrated in most aqueous solutions where it remains insoluble. Sephadex is composed of dextran cross-linked with epihydrochlorin, both of which are generally regarded as safe (GRAS) by the Food and Drug Administration. In addition, dextran microspheres are used in humans to treat wound infections (Debrisan) and fetal incontinence (Solesta) and is therefore most likely to be safe if used as a treatment for dental caries within the oral cavity.

Applicant also provides herein an assay to test the adherence of oral Streptococci to Sephadex where bacteria are grown in laboratory medium during exponential growth. For proof of principle, Applicant focused on *S. mutans*, but Applicant also tested a variety of other oral bacteria. An aliquot is removed and added to a microspin column containing Sephadex (125 µl final volume, containing laboratory medium or toxic cargo). After incubation for less than 5 minutes, the column is centrifuged for 1 min at 100×g to separate the Sephadex-bound and unbound bacteria. Only bacteria that have not adhered to the Sephadex will flow through and be collected. The amount of cells present in the flow through is measured by optical density at 600 nm or by serial dilutions followed by plating onto agar to determine colony forming units (CFU). Using this assay, Applicant demonstrates that a variety of *S. mutans* strains are readily able to attach to Sephadex in less than 10 seconds. This adherence was specific to *S. mutans* and other *mutans* streptococci since Applicant did not observe measurable binding using bacterial strains (*Escherichia coli, Lactobacillus acidophilus, Lactobacillus salivarius*) that do not produce glucosyltransferases. Using microscopy Applicant can visually observe *S. mutans* attached to the Sephadex, whereas *E. coli* does not bind.

Applicant's novel approach in using Sephadex to eliminate cariogenic and opportunistic bacteria includes loading the Sephadex microsphere lumen with toxic cargo. This allows the targeted killing of bacteria that have bound to the resin. Applicant initially used two antimicrobial agents commonly found in oral health care products; hydrogen peroxide and chlorhexidine. Compared to exposure with hydrogen peroxide and chlorhexidine alone (no Sephadex), when *S. mutans* was incubated with the same concentration of toxic cargo but loaded into Sephadex, a greater proportion of bacteria were eliminated in Applicant's assay. This was the case in both the bacteria recovered from the flow through and those recovered from the Sephadex resin. The opposite results were seen with *E. coli* where no bacteria were recovered when exposed to hydrogen peroxide and chlorhexidine alone, but in the presence of toxic-cargo loaded Sephadex, significantly more bacteria were recovered, suggesting that since the *E. coli* does not bind to the beads, the cells were protected from the antimicrobial agents. These experiments provide evidence where using Sephadex containing toxic cargo targets and eliminates cariogenic bacteria and opportunistic pathogens while leaving the normal microbiota minimally disturbed.

Experimental

Bacterial Strains and Growth Conditions.

Table 1 lists the bacterial species and strains used in this study. Each strain was grown in their appropriate growth media and growth conditions according to the references given. The UA159 gtfBCD deletion strain was constructed by insertion of erythromycin and tetracycline cassettes by allelic exchange using genomic DNA from the GS-5 gtfBC double mutant (Hanada, N. et al. (1989) Infect Immun 57:2079-2085) and the GS-5 gtfD single mutant (Hanada, N. et al. (1989) Infect Immun 57:2079-2085) respectively. Genomic DNA from these mutant strains was purified using the Masterpure Gram-positive DNA Purification Kit (Epicentre, Madison, Wis.). To introduce DNA from the gtfBC mutant, a UA159 wild type culture was grown to mid-exponential phase ($OD_{650nm}$ 0.5) in a chemically defined medium (van de Rijn, I. et al. (1980) Infect Immun 27:444-448), followed by the addition of 1 µg gtfBC genomic DNA and 1 µM XIP pheromone to induce natural transformation (Mashburn-Warren, L. et al. (2010) Molecular Microbiology 78:589-606). The culture was incubated at 37° C. for 3 hours followed by plating onto THB agar containing 1.5 µg/ml erythromycin. To construct the triple gtfBCD deletion strain, genomic DNA from the GS-5 gtfD mutant was introduced into the UA159 gtfBC mutant as described above, except transformants harboring the gtfBCD deletion were selected by plating onto THB agar containing 4 µg/ml tetracycline.

Sephadex (DM) Assay.

*S. mutans* (UA159) overnight cultures were diluted into fresh Todd Hewitt Broth (THB; BD Bacto, Fisher Scientific) with and without 3% sucrose and grown at 37° C. under 5%

$CO_2$ while growth was monitored at $OD_{650nm}$ (Ajdic, D. et al. (2002) PNAS 99:14434-14439). Once the culture reached the specified $OD_{650nm}$, 0.5 ml of culture was added to a Micro Bio-Spin chromatography column (BioRad, Hercules, Calif.) containing 250 µl of a 10% slurry (w/v) of Sephadex (Sciences GHL (2014) Sephadex Size Exclusion Media. [Online.]) (125 µl final volume; 12.5 mg). DM was prepared by hydrating in THB, followed by autoclaving. Cells and DM were incubated at room temperature (RT) at the indicated times and then unbound cells were harvested by centrifugation at 100×g for 1 min unless described differently in the text. To calculate the percentage of unbound cells, the $OD_{650nm}$ of the cells that eluted from the column were measured. For each condition a parallel reaction without DM was set to 0% for comparison.

For DM adherence assays with pooled human saliva (Lee Biosolutions, Maryland Heights, Mo.), overnight cultures of S. mutans UA159 were diluted into fresh THB with and without 3% sucrose and grown at 37° C. with 5% $CO_2$ until early log phase ($OD_{650nm}$ 0.3). Differing amounts of saliva were added to the culture as indicated and cells were incubated at RT for 30 min. followed by the DM spin column assay described above.

Mixed culture Sephadex (DM) assay. S. mutans (MW30 (Desai, K. et al. (2012) Journal of Bacteriology 194:3774-3780)) and S. gordonii (CH1) overnight cultures were diluted into fresh THB and grown at 37° C. under 5% $CO_2$ while growth was monitored at $OD_{650nm}$. Once the cultures reached early log phase growth ($OD_{650nm}$ ~0.3 for $10^8$ CFU) 250 µl of each culture (1:1 ratio) was mixed and added to a microspin column containing 250 µl of a 10% slurry (w/v) of DM (125 µl final volume; 12.5 mg) and incubated for 5 min. at RT and then unbound cells were harvested by centrifugation at 100×g for 1 min. For ratios of 1:100 S. mutans:S. gordonii, 2.5 µl S. mutans+247.5 µl THB and 250 µl S. gordonii were used and assayed as described above. The flow-through was serial diluted in PBS, and serial dilutions were plated onto THB+1.5 µg/ml Erythromycin (S. mutans) or THB (S. gordonii) agar and incubated at 37° C. +5% $CO_2$. S. gordonii grows fasters and has a different colony morphology and can be easily distinguished from S. mutans. For each condition a parallel reaction without DM was set to 100% for recoverable CFUs.

Biofilm Removal Assay.

Biofilms were seeded as described previously (Goodman, S. D. et al. (2011) Mucosal Immunol 4:625-637) with the following modifications. An overnight liquid culture of S. mutans UA159 was diluted to OD490 0.1 and grown statically at 37° C. under 5% $CO_2$ until an OD490 of 0.65 was reached. The culture was then diluted to OD490 0.05 in THB or THB+3% sucrose and 200 µl was seeded into wells of a MBEC™ Assay Biofilm Inoculator (Innovatech, Alberta, CA) 96-well plate containing hydroxy apatite coated pegs connected to the plate lid, and biofilms were grown at 37° C. under 5% $CO_2$ for 24 hours. For biofilm removal via DM in suspension, the pegs were rinsed twice with 200 µl PBS and then placed into wells of a 96 well plate containing THB or THB comprising 10% (w/v) DM slurry for 5 min. The suspension was then serially diluted and plated onto THB agar. The peg was then detached aseptically with needle nose pliers, placed into 200 µl of THB and sonicated in a water bath sonicator (Fisher Scientific FS20) for 10 min. The suspension was plated onto THB agar to determine the amount of cells retained on the peg. For DM biofilm removal via DM in agarose, the pegs were rinsed twice with 200 µl PBS and then placed into a 96 well plate containing THB or THB comprising 10% w/v DM in solidified 2% low melt agarose (IBI Scientific, Peosta, Iowa) for 5 min. The agarose was removed from the well and incubated at 37° C. for 10 min to melt the agarose. The melted suspension was serially diluted and plated onto THB agar. The peg was detached aseptically with needle nose pliers and placed into 200 µl of THB and sonicated in a sonicator water bath for 10 min. The suspension was plated onto THB agar to determine the amount of cells retained on the peg.

Scanning electron microscopy. S. mutans (UA159), S. gordonii (Challis CH1), S. cristatus (ATCC 49999), and E. coli (N99) were grown in THB (all streptococci) or LB (E. coli) to early exponential phase ($OD_{650nm}$-0.3) and 500 µl was added to a Micro Bio-Spin chromatography column containing 250 µl of a 10% slurry (w/v) of DM hydrated in THB (125 µl final volume; 12.5 mg). The cells and DM were incubated at room temperature (RT) for 5 minutes and unbound cells were harvested by centrifugation at 100×g for 1 min. The retained DM-cell mixture was kept in the column and fixed overnight at RT in 250 µl of 2.5% glutaraldehyde in 0.1M sodium phosphate buffer pH 7.2. The sample was then spun at 100×g for 30 sec. to remove excess glutaraldehyde followed by the addition of 250 µl 1% osmium tetroxide in 0.1M phosphate buffer pH 7.2. The mixture was incubated at RT for 1 hour and washed once with 250 µl distilled water for 5 min. and spun as above. The samples were then dehydrated using a stepwise gradient of 250 µl ethanol and water as follows. 50% ethanol for 15 min., 70% ethanol for 30 min., 95% ethanol for 15 min., 100% ethanol twice for 15 min. each with spinning at 100×g for 30 sec. between each addition. A 1:1 ratio (v/v) of ethanol:hexamethyldisilazane (2500 was added and incubated at RT for 100 min. and spun as above followed by the addition of 250 µl 100% hexamethyldisilazane for 15 min. Excess liquid was removed by spinning as described above and the dehydrated cell:DM mixture was dried overnight in the column at RT. The mixture was then mounted onto a 15 mm stub (Electron Microscopy Sciences, Hatfield, Pa.) using double sided carbon tape (Electron Microscopy Sciences, Hatfield, Pa.) and allowed to dry again overnight at RT. The samples were them sputter coated with 3 nm gold/palladium using a K550X Sputter Coater (Quorum Technologies, East Sussex). Samples were viewed with a Hitachi S-4800 Field Emission Scanning Electron Microscope.

Toxic Cargo.

DM was hydrated in THB only (control) or THB containing either hydrogen peroxide (1.5%) or chlorhexidine (0.2%) to create a 10% (w/v) slurry. For Applicant's DM assays, 250 µl of hydrated DM G25 superfine (125 µl final volume; 12.5 mg) was added to a Micro Bio-Spin chromatography column (BioRad, Hercules, Calif.) and excess liquid was removed by centrifugation at 100×g for 30 seconds, leaving DM with toxic cargo in the lumen. 125 µl of THB (the same volume of excess toxic cargo removed by filtration) was added to the DM column to create a 10% slurry (w/v), followed by the immediate addition of 500 µl of culture as described above for Applicant's basic DM assay. For control assays containing no DM, 125 µl of THB or THB containing toxic cargo (the same volume that is present in the DM lumen) was added to the spin column containing 125 THB followed by the addition of 500 µl of culture as described above for Applicant's basic DM assay. After incubation for 1 minute at RT, the cell/DM mixture was centrifuged for 1 minute at 100×g. The flow-through was serial diluted in PBS, and serial dilutions were plated onto THB (S. gordonii) or THB containing 1.5 µg/ml erythromycin (S. mutans) or LB (E. coli) agar and incubated at 37° C.+5% $CO_2$. To determine the amount of recoverable bacteria present associated with the beads after centrifugation, the DM was resuspended in a total volume of 750 µl THB and serial diluted in PBS. Dilutions were then plated onto THB agar and incubated at 37° C.+5% $CO_2$. For mixed culture experiments the assays were performed as described above. For sucrose assays, cultures were grown to early log phase as described above followed by the addition of 3% sucrose and incubated at 37° C. for 10 min. and then cultures were immediately used for the DM assay as described above.

Statistical Analysis.

Statistical significance was determined by unpaired t-tests (GraphPad Prism version 6.0) based on at least three separate experiments. P values are indicated by asterisks and are shown in the figure legends.

Results

Testing Different Sizes of Sephadex for Affinity Purification of S. mutans.

Based on the observation that Sephadex (dextranomer microspheres; DM) can bind glucosyltransferases (Mooser, G. et al. (1985) Journal of Biological Chemistry 260:6907-6915), and because these extracellular proteins are strongly associated with the bacterial surface, Applicant hypothesized that DM could be exploited and used as a therapeutic agent to specifically remove S. mutans cells from a culture, while leaving the healthy commensal microbiota minimally disturbed. To test Applicant's hypothesis, Applicant grew S. mutans UA159 to early logarithmic phase ($OD_{650nm}$ ~0.3), the peak of GTF expression (Goodman, S. D. et al. (1999) Plasmid 42:154-157; Goodman, S. D. et al. (2000) Plasmid 43:85-98) and added cells (~$10^8$ CFU) to a microspin column containing media (control) or a slurry of a variety of DM resins (Sciences GHL (2014) Sephadex Size Exclusion Media. [Online.]). After a 5 minute incubation, the unbound cells were harvested and compared to cells collected that were mixed with media only (no DM). Applicant observed that S. mutans was significantly partitioned to the DM resin with only a brief exposure to G-25 superfine, whereas no significant amount of S. mutans was retained from the culture with all of the other DM resins tested. (FIG. 1A). Strikingly, when the cells were grown in the presence of 3% sucrose (the substrate of S. mutans glucosyltransferases), >90% of S. mutans adhered to DM suggesting that synthesis of glucans was important for increased binding to DM (FIG. 1A). Furthermore, the addition of 3% glucose to the growth medium had no effect on S. mutans adherence indicating that increased binding to DM was specific to sucrose (data not shown). The fact that G-25 superfine was also the smallest size microsphere resin tested, suggests that the greater the partitioning of S. mutans cells to the bound state, is the result of the greater the surface area per weight resin. Therefore the smallest bead, G-25 superfine, was used in Applicant's assays for the remainder of this study.

Optimizing S. mutans/DM Binding Conditions.

Figure 1B:
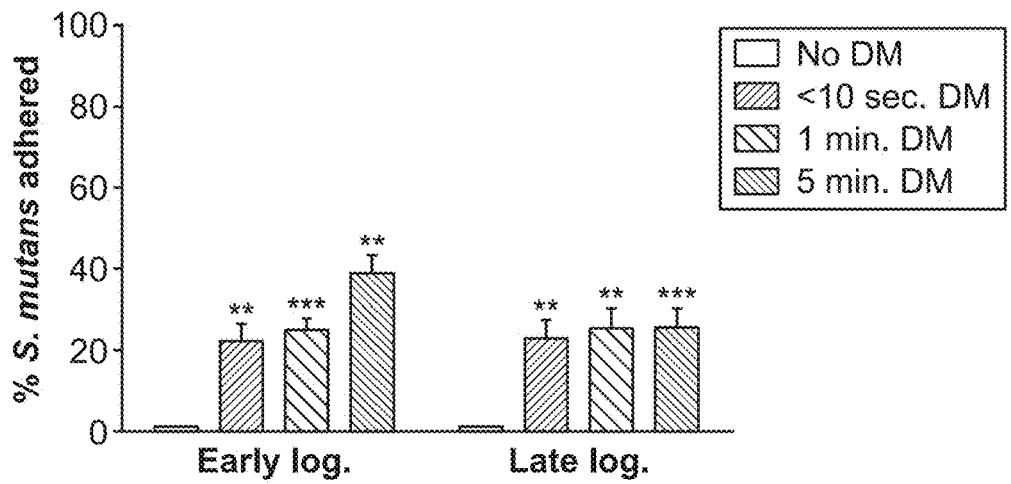
Figure 1C:
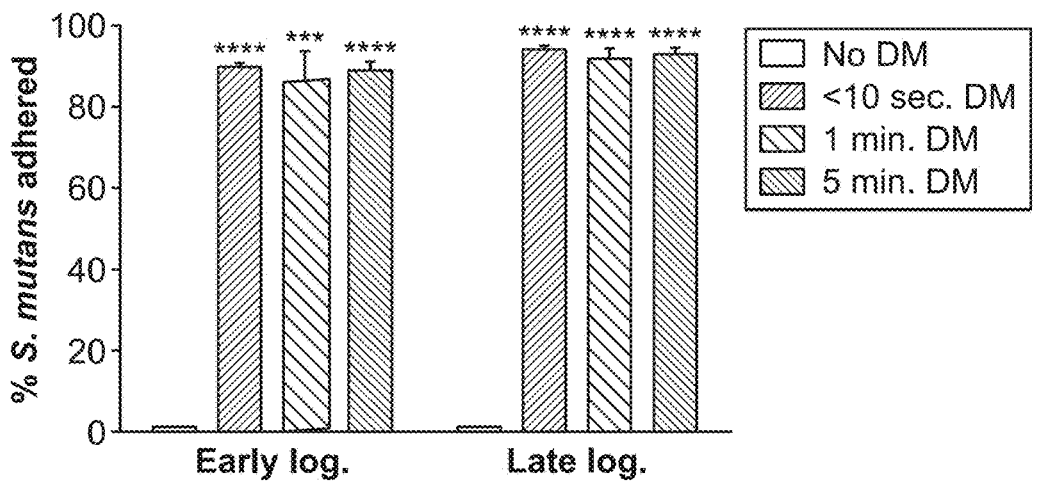

Applicant next investigated the rate of bacteria binding to DM and if the kinetics were affected by the growth phase of the S. mutans cells. S. mutans UA159 cultures were grown to either $OD_{650nm}$ 0.3 (early-log phase, ~$1\times10^8$ CFU) or 0.8 (late-log phase, ~$5\times10^8$ CFU) in the presence and absence of 3% sucrose before incubation with 0.125 ml (12.5 mg) DM for 0 to 5 min. (FIGS. 1B & 1C). In as little as 10 seconds a significant amount of binding had already occurred during logarithmic and late logarithmic phases of growth (FIG. 1B), where greater binding was seen in the presence of sucrose (FIG. 1C). Increased exposure to DM had no significant impact on the binding of S. mutans to DM (FIGS. 1B & 1C) within the time frame of Applicant's assay (5 min.) indicating that adherence of S. mutans to DM was a rapid event.

Figure 10A:
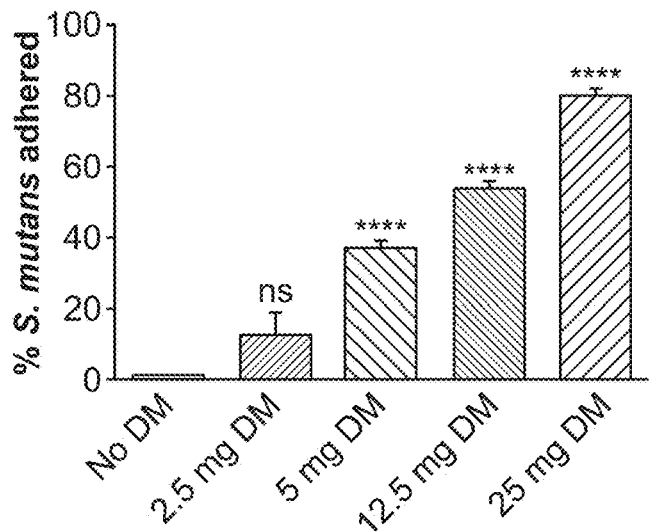
FIGS. 10A-10B show increased amounts of DM and exposure time to sucrose enhances the removal of S. mutans.
Figure 10B:
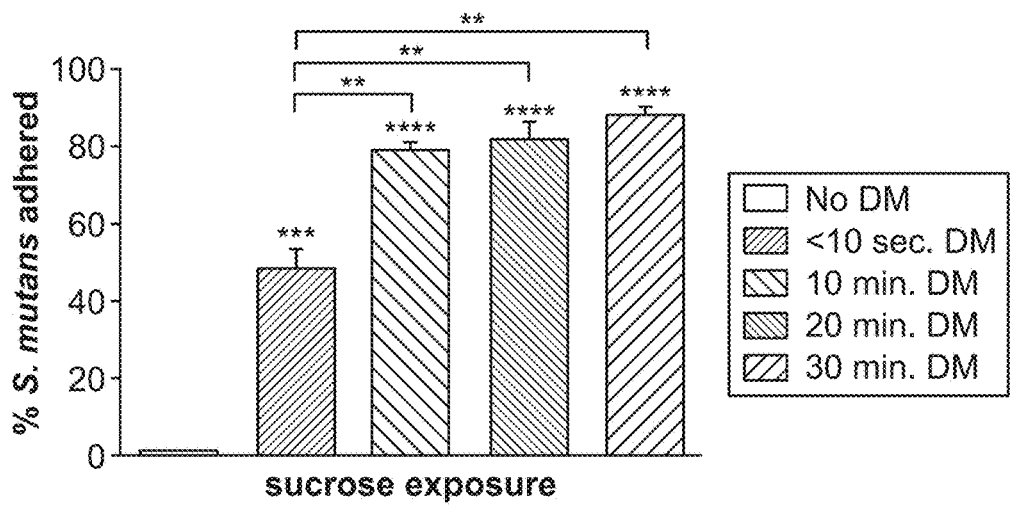

To determine if binding to DM was dose dependent, Applicant varied the amount of DM (10% slurry hydrated in THB) added to the assay. G-25 superfine DM was titrated from 0-25 mg and incubated with 0.5 ml S. mutans (~$10^8$ CFU) for 5 min. As expected, an increase of DM present in the assay resulted in more cells partitioning to the bound state, with the highest percent removed (>75%) with 25 mg DM after just 5 min. of incubation with S. mutans grown in THB (no sucrose) (FIGS. 10A-10B).

Given Applicant's results indicate that S. mutans was able to adhere to DM to a greater extent when grown continuously in the presence of sucrose Applicant also determined the rate at which brief exposure to sucrose would mediate attachment to DM, a condition more likely to be found in the oral cavity. S mutans was grown in THB to early-log phase ($OD_{650nm}$ 0.3, ~$10^8$ CFU) followed by the addition of 3% sucrose. Aliquots of the culture were then added to DM immediately (<10 sec.) or at various time points (10, 20, and 30 min.) after sucrose addition. S. mutans adherence was saturated in as little as 10 min, where >80% of S. mutans was bound, with no significant increase in DM binding was observed when S. mutans was exposed to sucrose for longer time periods (20 and 30 min.) (FIG. 10B).

Various S. mutans Wild Type and Mutant Strains Assayed for Binding to DM.

Figure 2A:
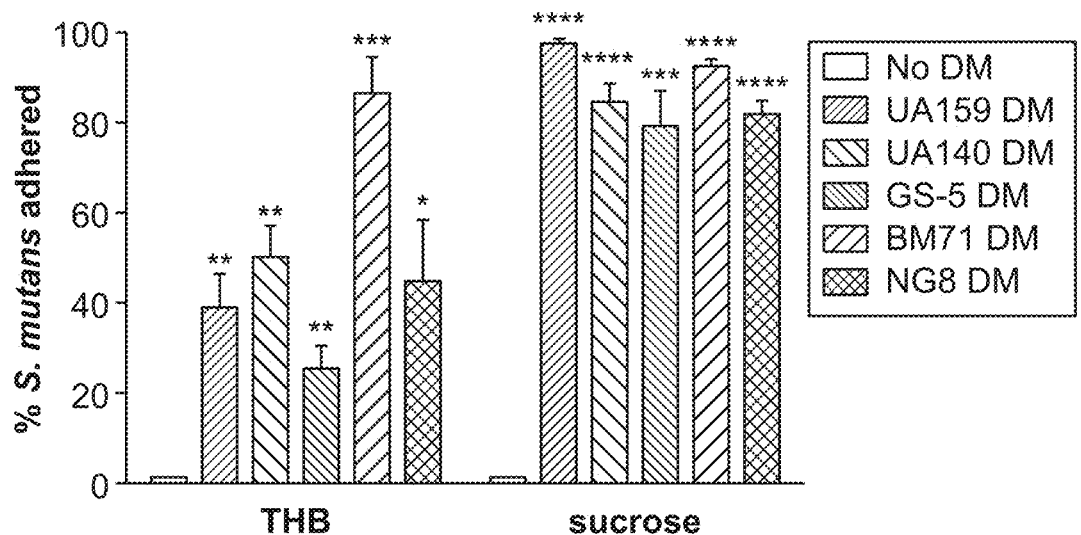
FIGS. 2A-2B show specificity of DM for various *S. mutans* wild type strains and glucosyltransferase mutants.

The complexity of the S. mutans flora found in some individuals can have as many as 5 different strains within their oral cavity (Kulkarni, G. V. et al. (1989) Journal of Dental Research 68:1155-1161). To confirm that this assay is applicable to other S. mutans strains, five laboratory wild type (WT) strains (UA159, UA140, GS-5, NG8, & BM71), and 2 mutant strains (UA159::gtfBCD⁻ & GS-5::gtfBCD (Hanada, N. et al. (1989) Infect Immun 57:2079-2085)) were tested in Applicant's assay. GtfB, GtfC and GtfD are glucosyltransferases that convert sucrose to sticky glucan polymers that facilitate the S. mutans ability to stick to teeth. Moreover, DM-like resin has previously been used for glucosyltransferase purification (Mooser, G. et al. (1985) Journal of Biological Chemistry 260:6907-6915). Each strain was tested for binding to DM as follows. Cultures were monitored until they reached early log phase ($OD_{650nm}$ ~0.3), prior to exposure to DM (0.5 ml culture, ~$10^8$ CFU) with or without adding 0.25 ml of a 10% slurry (w/v) of DM G-25 superfine incubated for 5 min. As shown in FIG. 2A, all WT S. mutans strains partitioned significantly to DM from culture. In addition, growth in sucrose greatly enhanced the adherence of S. mutans to DM in all strains tested demonstrating that all WT strains of S. mutans behaved similarly in their capacity to bind DM (FIG. 2A).

Figure 2B:
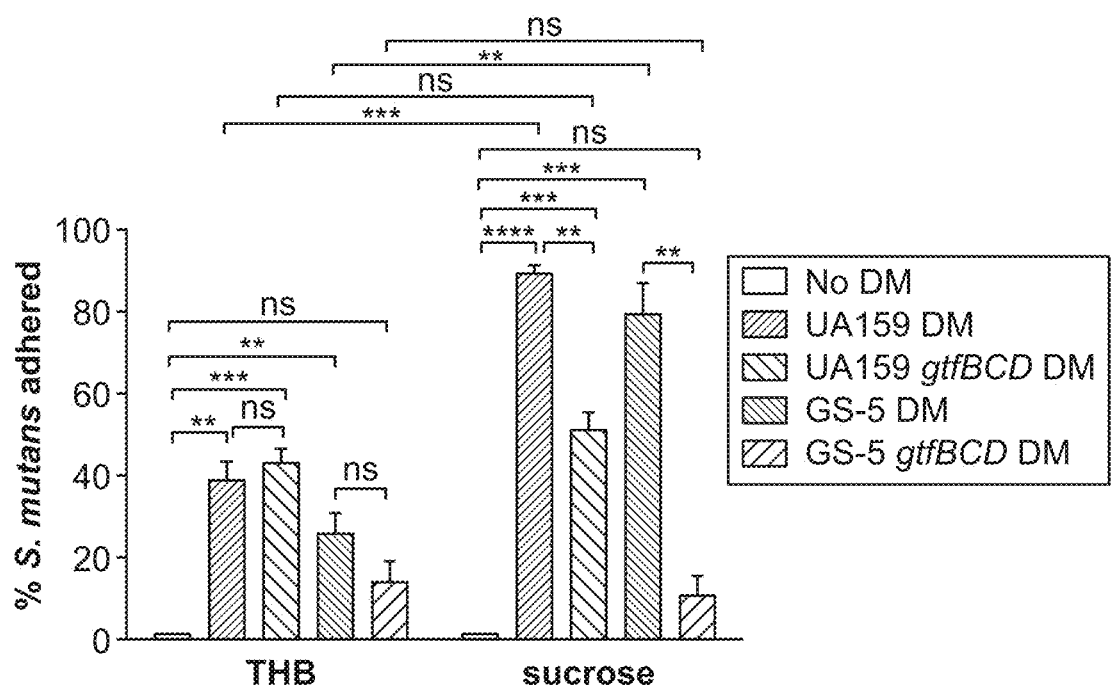
Figure 3A:
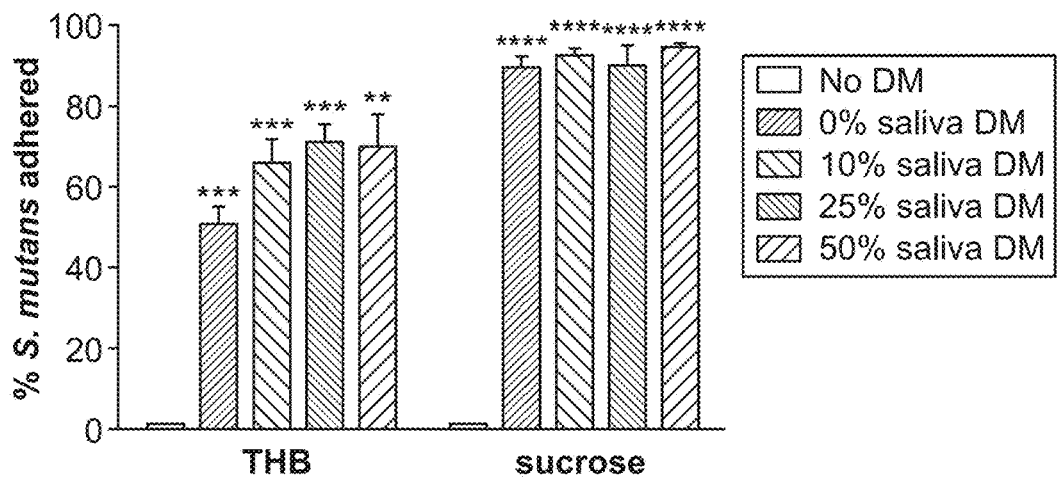
FIGS. 3A-3C show adherence of *S. mutans* to DM under conditions encountered in the oral cavity. *S. mutans* UA159 was grown in THB or THB+3% sucrose with differing amounts of human saliva (FIG. 3A), varying pH (FIG. 3B), or a range of SDS concentrations (FIG. 3C) and incubated for 5 min. without and with 125 μl (12.5 mg) G-25 superfine DM. The percentage of cells adhered to DM was calculated for each condition compared to without DM (set at 0%). Error bars represent the standard error mean (SEM). Asterisks indicate the statistical significance of assays performed with DM vs. no DM ($P<0.007$; *$P<0.001$; ****$P<0.0001$).
Figure 3B:
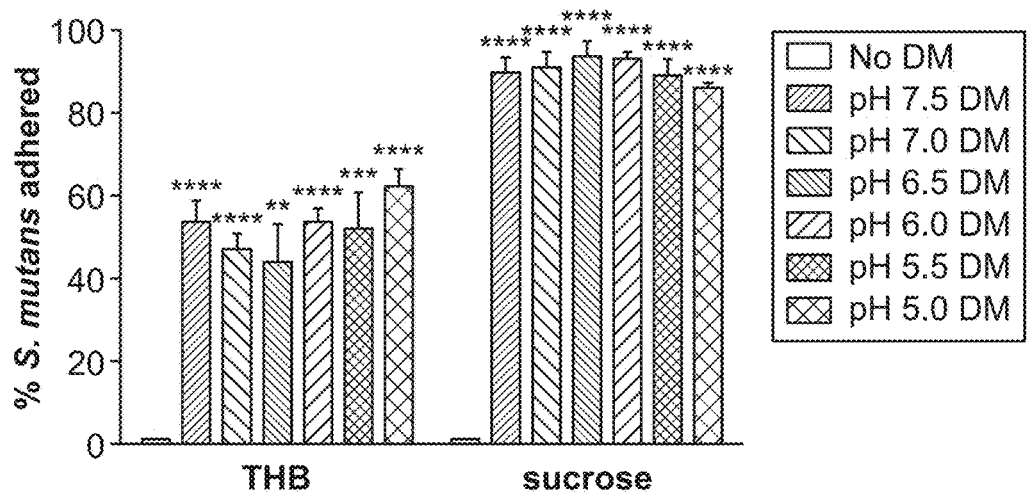
Figure 3C:
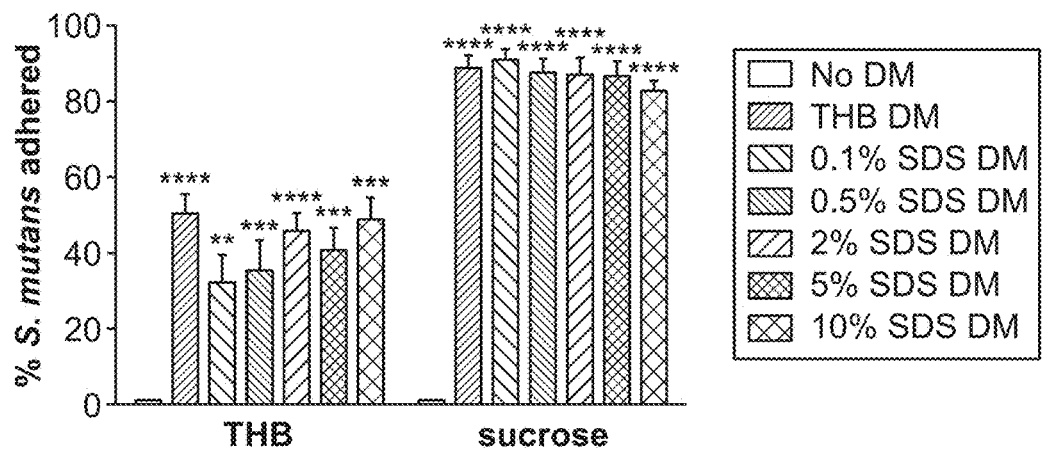

In the UA159 gtfBCD deletion mutant, no significant difference in DM binding was observed when cells were grown in THB (FIG. 2B). However in the presence of 3% sucrose when compared to the WT, significantly less UA159 gtfBCD mutant cells partitioned with the DM (FIG. 2B). In contrast to the GS-5 WT, the GS-5 gtfBCD mutant strain displayed no significant adherence to DM even when grown in the presence of sucrose (FIG. 2B), signifying that the GTFs play an important role in DM binding and that the synthesis of glucan is also crucial.

S. mutans Adherence to DM Under Conditions Encountered in the Oral Cavity.

Figure 4A:
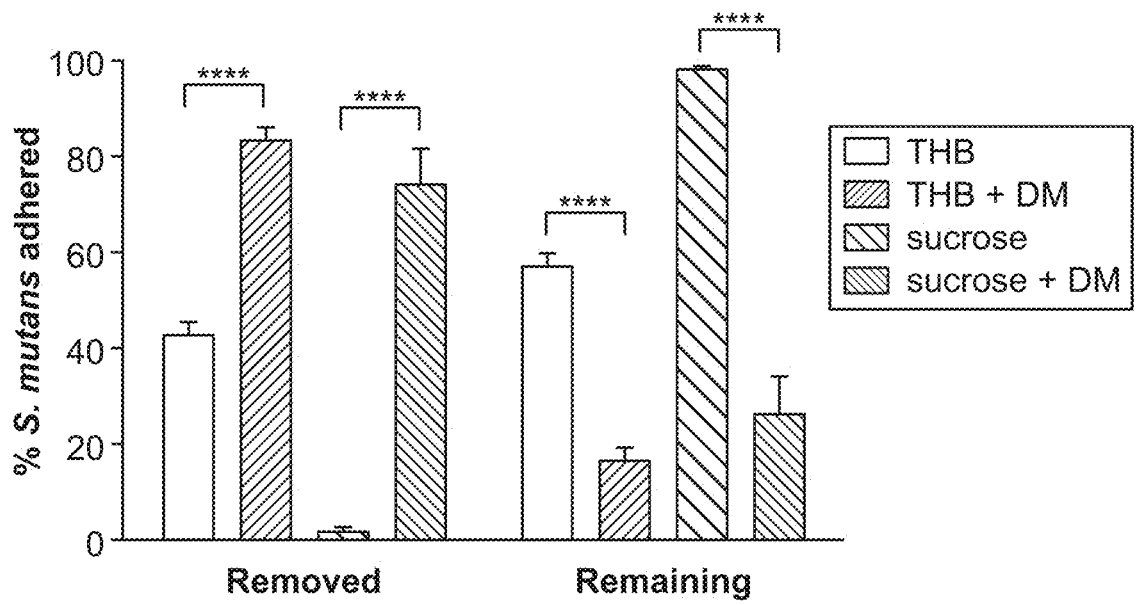
FIGS. 4A-4B show removal of *S. mutans* biofilms with DM. *S. mutans* biofilms were grown in THB or THB+3% sucrose for 24 hours in an MBEC™ Assay Biofilm Inoculator plate containing hydroxy appetite coated pegs. After 24 hours, the pegs were rinsed 2 times with PBS and placed into wells containing 125 μl (12.5 mg) DM G-25 superfine in suspension hydrated in THB (FIG. 4A) or in solidified 2% low melt agarose (FIG. 4B) for 5 min.
Figure 4B:
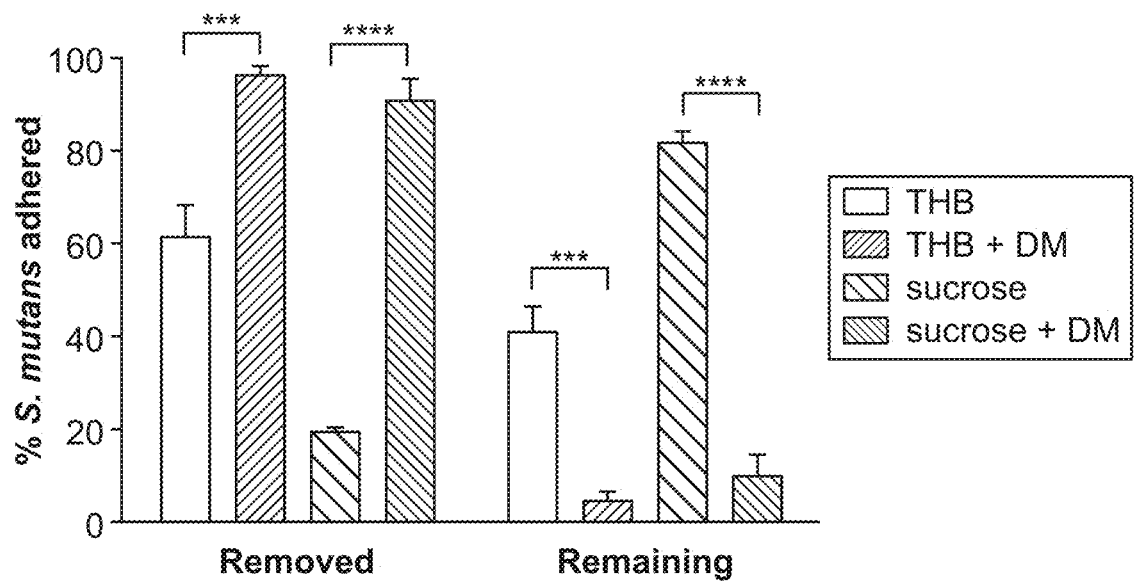

Within the oral cavity S. mutans combats a number of different environments such as saliva, low pH, and detergents (present in toothpaste and mouthwash) and Applicant wanted to examine the ability of S. mutans to bind DM under these conditions. To test this *S. mutans* was grown to early log phase ($OD_{650nm}$ of 0.3) and incubated with varying concentrations of pooled human saliva from healthy donors for 30 min. In addition *S. mutans* was grown in THB with varying pH or with a range of SDS concentrations. After growth to early log phase, Applicant applied the DM adherence assay with 500 μl of Applicant's *S. mutans* culture mixed with 250 μl of a 10% slurry of G25-SF DM (w/v). After incubating for 5 min. at RT, the mixtures were spun at 100×g for 1 min. and the percentage of cells that adhered to the DM was measured. Saliva, pH, and SDS had no impact on the ability of *S. mutans* to adhere to DM, where a significant amount of *S. mutans* had bound to DM, with even greater adherence when grown with sucrose (FIGS. 4A-4B). These observed results demonstrate that conditions commonly found in the oral cavity have no negative impact on the ability of DM to bind *S. mutans*.

Partitioning of *S. mutans* from Biofilms.

Thus far all of the DM binding assays were performed with planktonic (free-living) cells. Within the oral cavity *S. mutans* more typically resides on the surface of teeth in the form of a biofilm, a community of cells attached to a surface surrounded by a self-produced polymeric matrix. Because bacteria adhered to teeth in the biofilm state makes up the reservoir of oral microbes, Applicant wanted to determine the capacity of *S. mutans* to partition to DM from a biofilm adhered to a surface that closely resembles the tooth. To test this, Applicant grew *S. mutans* biofilms for 24 hours in THB and THB+3% sucrose on hydroxy apatite (HA) coated pegs (Innovotech) connected to a 96-well plate lid and performed an assay with a 10% slurry (w/v) with G-25 superfine DM (125 μl final volume; 12.5 mg) in suspension (THB). After rinsing the *S. mutans* biofilm coated pegs with PBS to remove non-adhered cells, the pegs were placed in a 96-well plate containing 200 μl THB (control) or the THB-DM suspension. This suspension was created to mimic a practical application such as mouthwash or toothpaste. After incubating the biofilms for 5 min. at RT, the suspension was serially diluted and plated to determine the amount of *S. mutans* that was removed from the biofilm. In addition, the peg was detached from the plate lid and placed in 200 μl THB and sonicated for 10 min. followed by serial dilution and plating on THB agar to measure the amount of bacteria that remained on the pegs after DM treatment. As shown in FIG. 4A, the DM in suspension removed a significant amount of the biofilm when grown in THB or THB in the presence of sucrose. Furthermore, significantly less *S. mutans* remained adhered to the HA coated pegs after DM treatment compared to biofilms treated with the media control.

To test another practical application for using DM for the prevention and treatment of dental caries, Applicant performed the same biofilm assay with DM present in agarose to simulate gum. Biofilms were grown for 24 hours on HA coated pegs as described above and placed in solidified 2% low melt agarose without and with 10% (w/v) G-25 superfine DM (125 μl final volume; 12.5 mg). Pegs were incubated in the agarose mixture for 5 min. at RT. The agarose was removed and incubated at 37° C. for 10 min. to allow the agarose to melt and subsequently was serially diluted and plated onto THB agar to quantify the number of bacteria detached from the biofilm. Following DM treatment the peg was removed from the lid and the amount of remaining adhered bacteria was determined as described above. When treated with DM suspended in agarose, the biofilm bacteria readily and significantly partitioned with the DM compared to agarose without DM (FIG. 4B). Together these results demonstrate that DM can be used to eliminate *S. mutans* that exist in its native bound state.

Partitioning of Other Bacterial Species to Sephadex.

To use DM as an efficient method for the treatment of dental caries it would be ideal to specifically deplete the caries-causing bacteria with minimal disturbance/removal of the remaining commensals. Applicant utilized the column-based assay to test a broad range of oral bacteria to determine binding specificity to DM. As shown in Table 2, *S. sobrinus* (pathogen associated with dental caries) demonstrated the greatest partitioning to the DM, whereas other non-invasive and probiotic strains *Streptococcus thermophilus*, *Streptococcus cristatus*, *Streptococcus salivarius*, and *Lactobacillus acidophilus* exhibited the least amount of attachment to DM. Other oral streptococci that are known to be commensals within the oral cavity, but also have been shown to be opportunistic pathogens (*Streptococcus oralis*, *Streptococcus mitis*, *Streptococcus gordonii*, and *Streptococcus sanguinis*) also bound to DM with varying affinities (Table 2). Importantly, while sucrose caused enhanced binding of *S. mutans* (>80%) to the DM, sucrose had no significant impact on DM binding with any of the bacterial species tested using Applicant's assay.

Visualization of Oral Bacteria Bound to DM Beads.

Figure 11A:
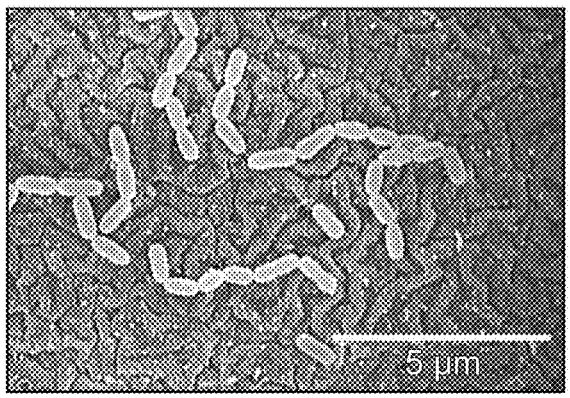
FIGS. 11A-11B show scanning electron microscopy of S. mutans wild type bound to DM. S. mutans WT was grown to early log phase ($OD_{650nm}$ ~0.3) and were then incubated without and with 125 µl (12.5 mg) G-25 superfine DM. Bacterial cells were grown in the absence (FIG. 11A) and presence of sucrose (FIG. 11B). The bacteria/DM mixture was fixed in glutaraldehyde overnight followed by staining with osmium tetroxide and then dehydrated with a stepwise gradient of ethanol and hexamethyldisilazane and dried overnight. The bacteria/DM mixture was mounted on 15 mm stubs with double sided carbon tape and sputter coated with palladium/gold. Samples were imaged using a Hitachi S-4800 Field Emission Scanning Electron Microscope. Higher magnification reveals glucan and cell-cell aggregation in the presence of sucrose (substrate for the glucosyltransferases) allowing a greater number of cells adhered to DM compared to growth without sucrose.
Figure 11B:
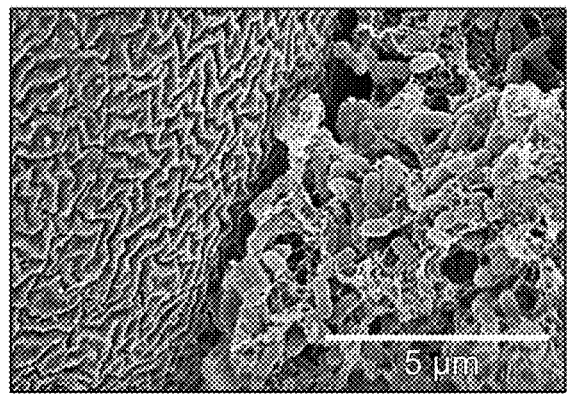

Applicant visualized the binding of oral bacteria by scanning electron microscopy (SEM). The DM from the Bio-Spin column assay were examined after equal numbers (~$10^8$ CFU) of *S. mutans*, *S. gordonii* (medium DM binder), *S. cristatus* (weak DM binder), and *E. coli* (non-DM binder) (Table 2) were grown in the presence and absence of sucrose and partitioned by centrifugation followed by visualization using SEM to examine cells bound to the DM. As seen in FIG. 5A, clusters of *S. mutans* WT are present and are found to be associated directly with DM when grown in THB. Strikingly, when *S. mutans* WT was grown in the presence of sucrose, substantial bacterial aggregates can be seen attached to and connecting individual DM (FIG. 5B). At higher magnification, cell-cell aggregation and glucan can be seen when WT was grown with sucrose compared to without sucrose (FIGS. 11A-11B). This aggregation required the synthesis of new glucan as the *S. mutans* ΔgtfBCD mutant did not display the same aggregation phenotype as the WT when exposed to sucrose. In fact in the presence of sucrose, the ΔgtfBCD mutant resembled WT, but was still able to bind DM as this strain still comprises at least 4 other non-GTF glucan binding proteins (Banas, J. A. et al. (2003) Critical Reviews in Oral Biology and Medicine: An Official Publication of the American Association of Oral Biologists 14:89-99). *S. gordonii* cells can be found attached to the DM although to a lesser extent than *S. mutans* (FIG. 5E). As expected, sucrose had no effect on *S. gordonii* partitioning to the DM (FIG. 5F). Both *S. cristatus* and *E. coli* showed little to no association with the DM (FIGS. 5G & 5I), even when sucrose was present (FIGS. 5H & 5J) demonstrating the specificity of *S. mutans* for the DM resin, predominantly when sucrose is present.

DM Exhibit a Higher Binding Affinity to *S. mutans* in Contrast to an Oral Commensal.

Figure 6:
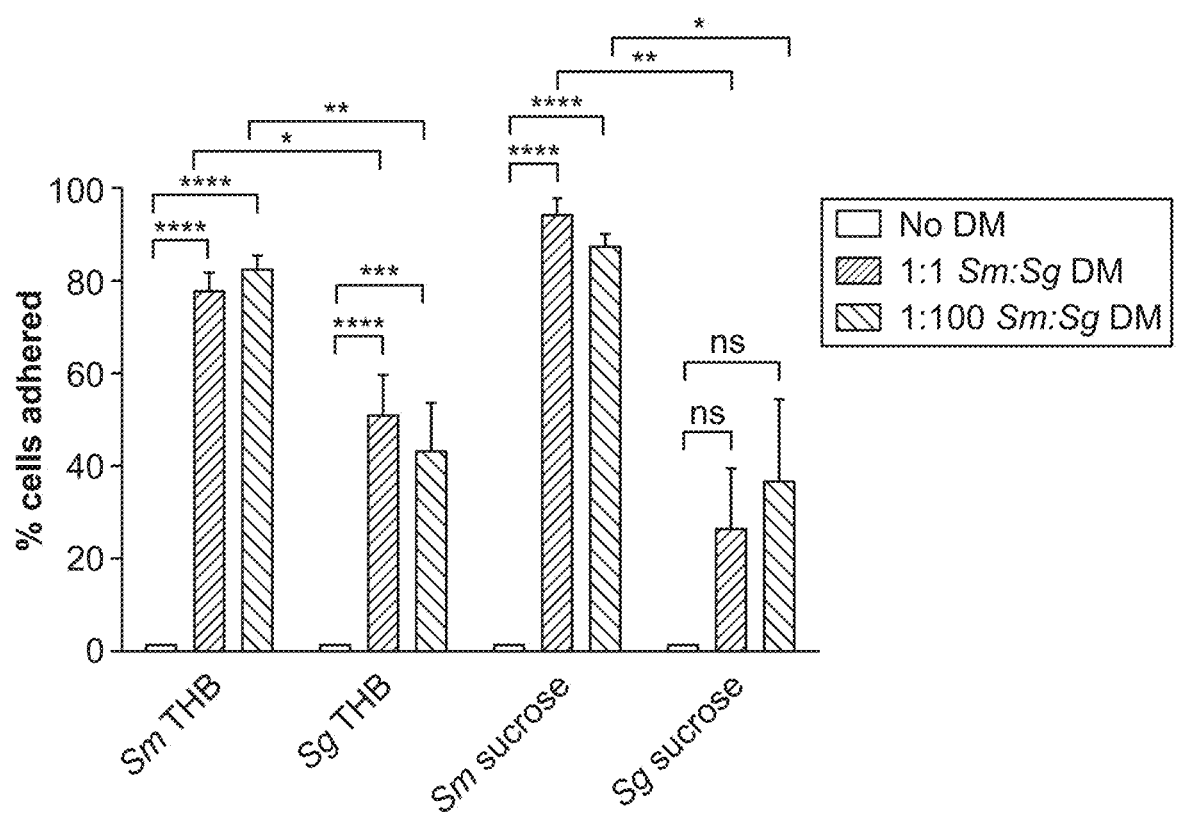
FIG. 6 shows *S. mutans* outcompetes *S. gordonii* for adherence to DM. *S. mutans* (MW30; $Erm^R$; (Desai, K. et al. (2012) Journal of Bacteriology 194:3774-3780)) and *S. gordonii* were grown in THB or THB+3% sucrose to early log phase and mixed together at 1:1 (*S. mutans* $10^8$ CFUs:*S. gordonii* $10^8$ CFUs) or 1:100 (*S. mutans* $10^6$ CFUs:*S. gordonii* $10^8$ CFUs) and incubated for 5 min. without and with 125 μl (12.5 mg) of G-25 superfine DM on a microspin column. Following centrifugation at 100×g for 1 min., the eluate for each culture was serial diluted and plated on selective plates. The percentage of cells recovered (not bound to DM) was calculated for each strain and compared to the absence of DM (set at 100%). Error bars represent the standard error mean (SEM). Asterisks indicate the statistical significance as designated by bars (*P<0.05; P<0.005; **P<0.0001; ns: not significant).
Figure 7A:
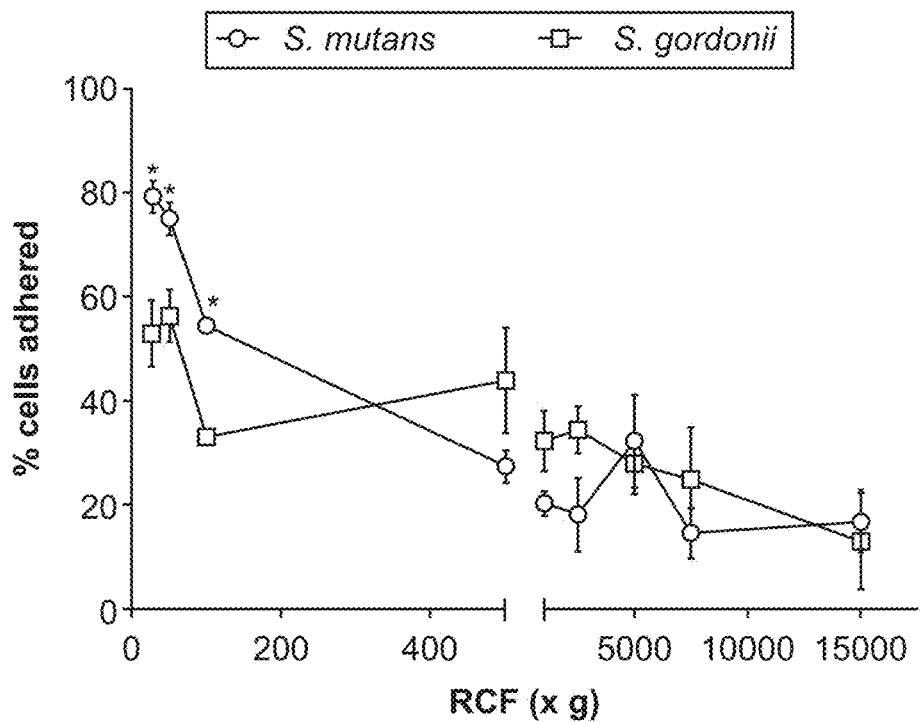
FIGS. 7A-7B show testing the binding affinities of S. mutans and S. gordonii to DM. S. mutans and S. gordonii (500 µl) were grown in THB (FIG. 7A) or THB+3% sucrose (FIG. 7B) to early log phase and incubated for 5 min. without and with 125 µl G-25 superfine DM. Following centrifugation at the indicated centripetal forces, the percentage of cells adhered to DM was calculated for each time point compared to without DM (set at 0%) for the same length of time. Error bars represent the standard error mean (SEM). Asterisks indicate the statistical significance of S. mutans vs. S. gordonii (*P<0.05 P<0.005; *P<0.001).
Figure 7B:
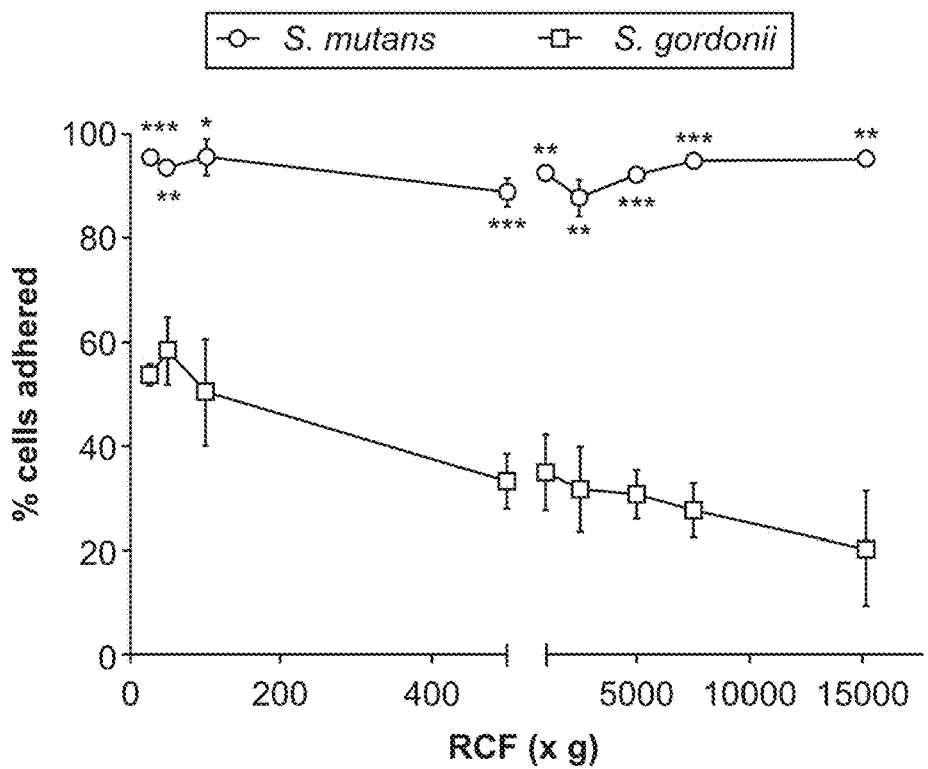

To better understand the potential of using DM to eliminate caries-causing bacteria with marginal effects on commensal bacteria, Applicant performed the binding assays utilizing mixed cultures with differing ratios of *S. mutans* and *S. gordonii* (an opportunistic pathogen and a modest DM binder) in the presence and absence of sucrose. Ratios of $10^8:10^8$ CFUs and $10^6:10^8$ CFUs *S. mutans*:*S. gordonii* were chosen to demonstrate the dynamic range of selectivity towards *S. mutans* over even a modest DM binder. When mixed together, *S. mutans* out-competed *S. gordonii* and partitioned to the DM to a greater extent under all conditions tested (FIG. 6). Unexpectedly, *S. mutans* adhered more efficiently to DM in the presence of *S. gordonii* even in the absence of sucrose. To gain more insight into the binding affinities of *S. mutans* and *S. gordonii* to the DM, Applicant completed the assays using a broad range of centripetal forces (27-15 k×g) using mono-species cultures with and without exposure to sucrose. As shown in FIG. 7A, *S. mutans* displayed a higher binding affinity to the DM compared to *S. gordonii* at lower g-forces, in the range of normal saliva tidal forces (Prakobphol, A. et al. (1995) Journal of Dental Research 74:1212-1218). This observation was further pronounced when *S. mutans* was subjected to growth in sucrose (FIG. 7B) where even the highest g-forces tested had no significant effect on binding disruption. As expected, sucrose had no impact on the binding affinity of *S. gordonii* to DM. This demonstrates that sucrose not only improves *S. mutans* binding kinetics but also dramatically stabilizes binding attachment to DM.

Supplying Bactericidal Cargo within the Lumen of DM.

Figure 8A:
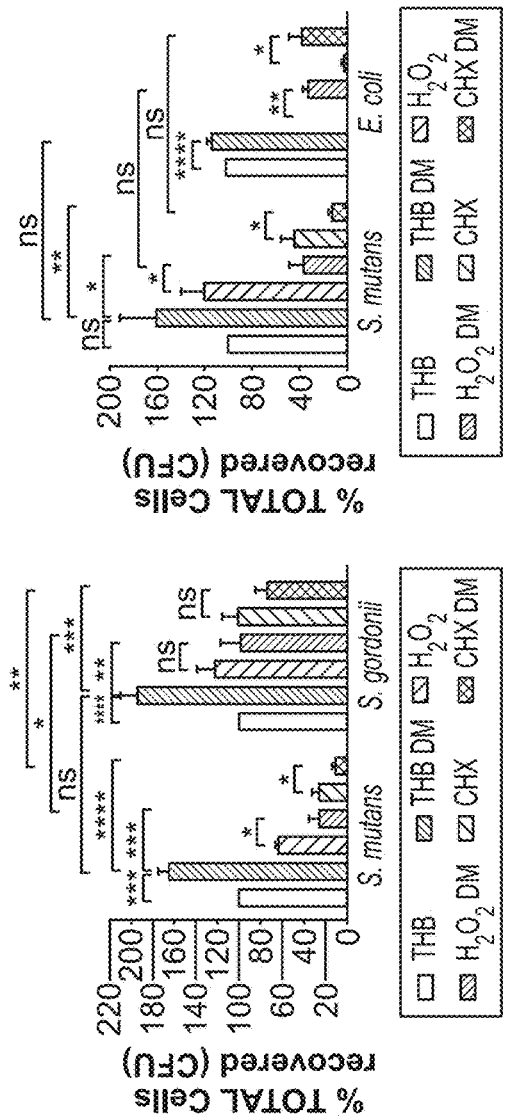
FIGS. 8A-8B show DM containing toxic cargo preferentially kills S. mutans while preserving S. gordonii and E. coli. (left panels) S. mutans ($10^6$ CFUs) (Erm$^R$; (Desai, K. et al. (2012) Journal of Bacteriology 194:3774-3780)), S. gordonii ($10^8$ CFUs) and E. coli ($10^8$ CFUs) were grown to early log phase without (FIG. 8A) or with (FIG. 8B) 3% sucrose as monocultures and exposed to DM containing media (THB), 1.5% hydrogen peroxide ($H_2O_2$) or 0.2% chlorhexidine (CHX) within the DM lumen or exposed to the same volume of toxic cargo without DM for 1 min. (middle panels) S. mutans ($10^6$ CFUs) (MW30; Erm$^R$; (Desai, K. et al. (2012) Journal of Bacteriology 194:3774-3780)) and S. gordonii ($10^8$ CFUs) or (right panels) S. mutans ($10^6$ CFUs) (MW30; Erm$^R$; (Desai, K. et al. (2012) Journal of Bacteriology 194:3774-3780)) and E. coli ($10^8$ CFUs) were mixed just prior to incubation with toxic cargo or toxic cargo contained within the DM lumen for 1 min. Non-bound cells and the DM/bacteria slurry that remained after centrifugation were plated to determine the total amount of recovered cells. The percentage of cells recovered when incubated with media (set at 100%) was compared to the amount recovered that was incubated with toxic cargo. Error bars represent the standard error mean (SEM). Asterisks indicate the statistical significance as designated by bars (*P<0.05; P<0.005; *P<0.001; ****P<0.0001; ns: not significant).

Not only does DM provide a surface for the binding and removal of *S. mutans*, it can also provide diffusible cargo within the lumen of the DM. By loading the DM with toxic cargo, Applicant speculated Applicant could both sequester *S. mutans*, and eliminate the cells that have attached. Applicant hypothesized that since other commensals bind to DM with varying affinities and to a lesser extent compared to *S. mutans* particularly when exposed to sucrose, the toxic cargo within the DM should display killing specificity to *S. mutans* and not the non-binding commensals. Applicant chose two antibacterial agents, chlorhexidine (CHX) and hydrogen peroxide ($H_2O_2$), found in a variety of oral health care products. Applicant created a slurry of G-25 superfine DM hydrated in these antimicrobial agents at the same concentrations typically found in oral healthcare treatments, 1.5% $H_2O_2$ and 0.2% CHX [12.5 mg DM (125 µl cargo volume) with an appropriate payload in 750 µl total volume]. Excess liquid was removed, keeping the toxic cargo within the DM lumen. The same volume was replaced with bacterial media and this slurry was then used in Applicant's assay as described above. Control assays were also performed without DM where the same quantity (volume) of CHX (0.033% final concentration) and $H_2O_2$ (0.25% final concentration) present as cargo within the DM were used. As shown in FIG. 8A (left panel), when grown in monoculture, the presence of CHX and $H_2O_2$ alone decreased the amount of total viable *S. mutans* and *S. gordonii* just after 1 min., whereas significantly more cells were killed when *S. mutans* was exposed to CHX and $H_2O_2$ in the form of DM cargo (FIG. 8A, left panel). Strikingly, Applicant observed no significant elimination of *S. gordonii* when cells were subjected to CHX or $H_2O_2$ when presented as toxic cargo within the DM compared to no DM exposure (FIG. 8A, left panel). Although fewer non-adhered cells of *S. gordonii* were recovered from the eluate (FIG. 12A, left panel), no significant amount of *S. gordonii* were killed when adhered to the DM when grown in mono-culture (FIG. 12B, left panel), making the total number of recoverable *S. gordonii* comparable to those treated with bacterial media (FIG. 8A, left panel). In contrast, *S. mutans* cells were drastically reduced in the eluate and were killed when attached to the DM (FIGS. 12A & 12B), making the total number of recoverable *S. mutans* cells significantly less compared to DM filled with bacterial media as cargo (FIG. 8A, left panel). In stark contrast to the results observed with *S. mutans*, when *E. coli* was treated with DM containing antimicrobial cargo, significantly more cells were recovered compared to cells exposed to the same volume of toxic cargo without DM, where >90% of *E. coli* cells were killed (FIG. 8A, left panel). This strongly suggests that one, non-binding bacteria will be spared from antimicrobials in the lumen of DM and two that the contents of the DM lumen fail to significantly diffuse into the bulk medium in this time frame, and three that *S. gordonii* is more resistant to the toxic cargo used in Applicant's assays at over-the-counter relevant concentrations. This further suggests that higher concentrations of antimicrobials could be loaded into the lumen of the microspheres for more efficient targeted killing.

Figure 8B:
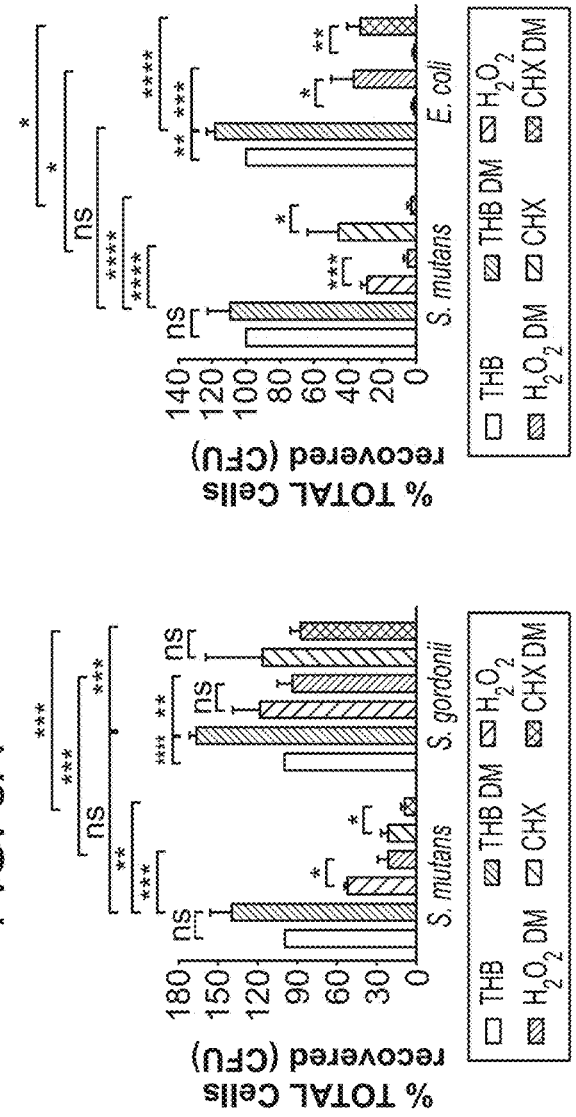
Figure 12C:
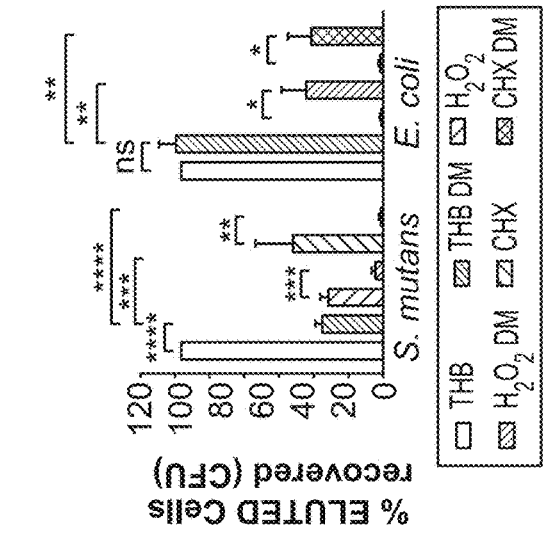
Figure 12C:
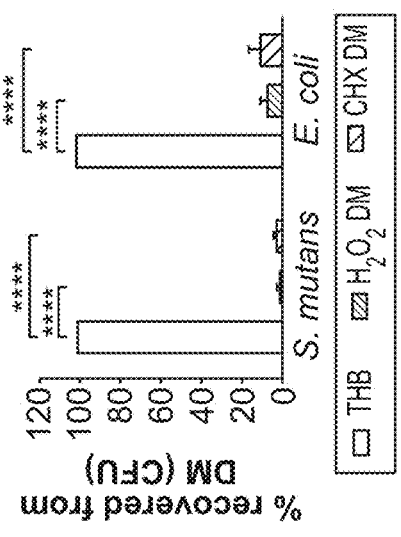
Figure 12D:
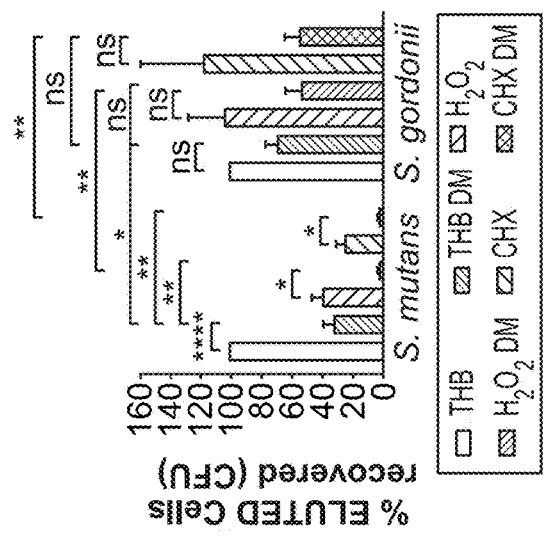
Figure 12D:
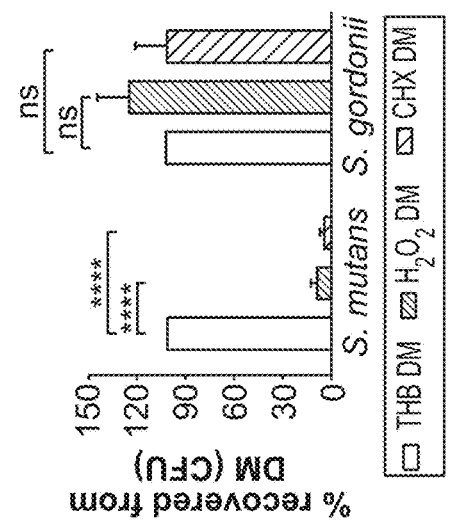
Figure 12D:
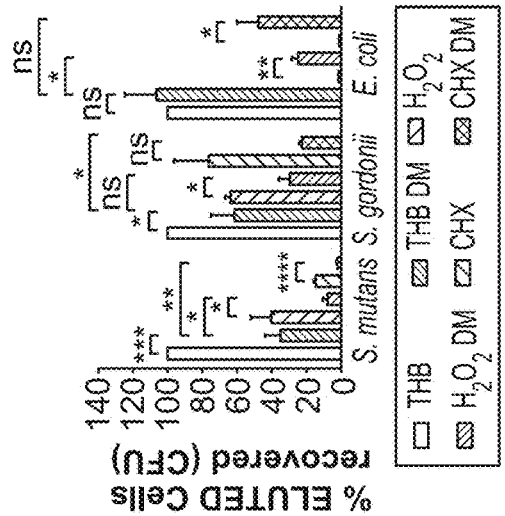
Figure 12D:
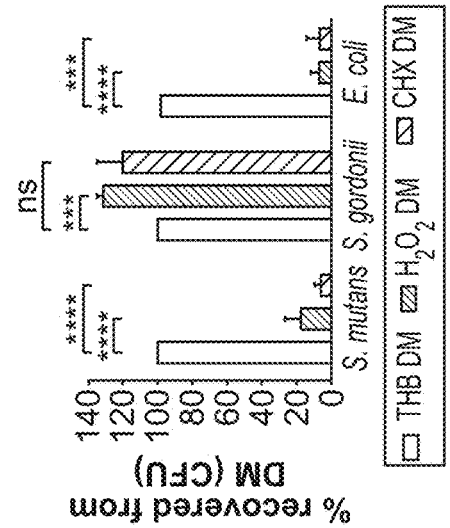

Based on Applicant's results of the monoculture assays with supplying antimicrobial agents as cargo within the DM lumen, Applicant wanted to investigate the ability of removing/killing the cariogenic bacteria while leaving an oral commensal and *E. coli* (non-binding as proof of principle) minimally disturbed within a mixed culture. To examine this Applicant used the assay described above but with a mixed culture of *S. mutans:S. gordonii* and *S. mutans:E. coli* where a marked strain of *S. mutans* [(MW30; Erm$^R$ (Desai, K. et al. (2012) Journal of Bacteriology 194:3774-3780)] was used at a 1:100 ratio again to demonstrate the dynamic range of selectivity of *S. mutans* to the DM resin. As shown in FIG. 8A (middle panel), the total percent of recoverable *S. gordonii* was significantly greater compared to *S. mutans*. In addition, when examining the amount of *S. gordonii* cells recovered in the eluate (non-adhered bacteria) there was no significant difference between the control (bacterial media) and the presence of $H_2O_2$ or CHX within the DM, whereas a significant percentage of *S. mutans* was not recovered (FIG. 12A, middle panel). Likewise, the percentage of *S. mutans* killed that had adhered to the DM was substantially greater than that of *S. gordonii* (FIG. 12B, middle panel). Applicant observed the same results with *E. coli* that Applicant obtained in the monoculture experiment described above where the DM provided a protective effect to these non-binding cells whereas *S. mutans* was killed in significant numbers (FIG. 8A, right panel). In addition these same results were also observed in mono and mixed cultures of *S. mutans:S. gordonii* and *S. mutans:E. coli* at ratios of 1:100 when exposed to sucrose (FIG. 8B) as well as with mono and mixed cultures of *S. mutans:S. gordonii* and *S. mutans/E. coli* at a 1:1 ratio with and without sucrose (data not shown). These results indicate that DM allow the targeted killing and removal of a cariogenic species while leaving an oral commensal and potentially other non-binding healthy commensals only marginally disturbed within a mixed population.

DISCUSSION

There is a continuing need for the development of new treatment strategies and therapeutics for the prevention of dental caries, where >90% of the adult population are effected. Currently, all the prevention methods in use are non-selective, broad-spectrum and do not distinguish between the different bacterial species found in the oral cavity. The ability of Sephadex to separate macromolecules without an applied electrical current, but rather based on size, was the observation of Professor Jerker Porath (Uppsala University, Sweden) after a mistake was made by a young scientist in his lab (Sciences GHL (2014) Sephadex Size Exclusion Media. [Online.]). Using DM, Mooser et al. (Mooser, G. et al. (1985) Journal of Biological Chemistry 260:6907-6915) was the first to demonstrate that the GTFs from *S. mutans* could be purified; in fact binding of GTFs to DM is nearly irreversible. Moreover, GTFs are strongly associated with the *S. mutans* bacterium itself (Kuramitsu, H. K. et al. (1978) Infection and immunity 20:652-659). Based on these observations, Applicant hypothesized that whole cells of *S. mutans* would preferentially bind to DM due to the localization of GTFs on the cell surface. Applicant's goal was to investigate the possibility of using DM to selectively deplete *S. mutans*, while not disrupting the normal microbiota, creating a less pathogenic and healthier oral cavity. Indeed, Guo et al. has recently shown, that transient depletion of *S. mutans* from the oral cavity resulted in the restoration of a less cariogenic microbiota (Guo, L. et al. (2015) Proceedings of the National Academy of Sciences of the United States of America 112:7569-7574).

In this study Applicant found that DM is able to bind *S. mutans* rapidly (<10 seconds) and independent of growth phases (early and late log phase) and growth states (planktonic and biofilm) in the presence or absence of sucrose. G25-superfine, the smallest DM resin commercially available, exhibited the best adherence to *S. mutans* in Applicant's assay. This was not surprising as the smaller the bead, the greater the surface to volume ratio. Furthermore, Sephadex resin pore size differs based on the degree of cross-linking, making it plausible that this DM resin allowed the greatest binding of *S. mutans*' GTFs compared to the other resins tested. Serotype c strains comprise the majority (>70%) of *S. mutans* strains found in the oral cavity (Nomura, R. et al. (2014) Infection and Immunity 82:5223-5234). The DM resin was able to remove a significant amount of various serotype c strains from the culture with Applicant's assay, although with differing degrees. This observation is not surprising as these strains likely produce different amounts of GTFs and glucan binding proteins and may vary their ability to aggregate. Nonetheless, just 12.5 mg of G-25 superfine, was able to eliminate >$10^7$ *S. mutans* cells under Applicant's assay conditions which is considerably more *S. mutans* than is typically present in human saliva ($10^6$/ml) (Guo, L. et al. (2013) Journal of the California Dental Association 41:107-109, 112-108).

In the oral cavity, *S. mutans* encounters a number of different conditions including the presence of saliva, low pH, and a number of ingredients found in oral health care products. Saliva comprises a neutral pH and keeps the mouth warm and moist and importantly provides the oral microbiome with nutrients. Within dental plaque biofilms where *S. mutans* resides, the pH can fluctuate especially after sugar intake where the pH can drop to around 4 (Lemos, J. A. et al. (2005) Current Issues in Molecular Biology 7:95-107). *S. mutans*' ability to proliferate and adapt to low pH allows it an advantage to other microorganisms within the biofilm. In addition *S. mutans* is exposed to a number of inhibitory ingredients found in toothpaste and mouthwash including SDS. Using their DM adherence assay, Applicant reveals that saliva, pH, and SDS had no negative impact on the ability of *S. mutans* to bind DM, supporting the use of DM to treat *S. mutans* and prevent dental caries under normal host conditions. Importantly, within the oral cavity, *S. mutans* grows predominantly in the form of a biofilm and here Applicant demonstrates that DM was able to readily bind *S. mutans* biofilms and detach them from a surface that closely mimics the tooth (FIGS. 4A-4B). Applicant examined *S. mutans* biofilm removal two ways to mimic real world applications; DM in suspension to simulate mouth wash and DM encased in agarose to imitate gum. Gum itself has adhesive properties in entrapping bacteria and removing them from the oral cavity. Wessel et al. recently revealed that ~$10^8$ bacteria were found in a single piece of gum, although both healthy and pathogenic bacteria are removed with no specificity towards oral pathogens (Wessel, S. W. et al. (2015) PloS One 10:e0117191). Applicant's new finding proposed here would allow an advantage to current chewing gums where Applicant could potentially target cariogenic and pathogenic oral bacteria while leaving the healthy oral commensal population minimally perturbed.

Sucrose significantly increased *S. mutans* binding to DM in Applicant's assays, where Applicant observed saturated binding in as little as 10 minutes following sucrose exposure. *S. mutans* employs three glucosyltransferases (GtfBCD) that utilize sucrose as a sole substrate to synthesize glucan, a sticky polymer of glucose that allows for efficient attachment to the surface of the tooth. In the *S. mutans* strain UA159, a triple mutant in gtfBCD displayed decreased binding to DM in the presence of sucrose in Applicant's assay, demonstrating the importance of these proteins in DM binding. Applicant observed an even more profound effect with *S. mutans* GS-5 gtfBCD, where a significant amount of bacterial cells did not partition with the resin compared to WT even when grown in the presence and absence of sucrose. GS-5 has natural deficiencies in gbpC and pac, encoding the cell wall-anchoring glucan binding protein C and a cell wall-anchored major protein antigen respectively. *S. mutans* has at least four non GTF-glucan binding proteins (GBPs, GbpABCD), all of which seem to be involved in virulence, but have distinct properties and functions. GbpB displays peptidoglycan hydrolase activity, and appears to be essential (Banas, J. A. et al. (2003) Critical Reviews in Oral Biology and Medicine: An Official Publication of the American Association of Oral Biologists 14:89-99). GbpA and GbpD are both secreted and share glucan binding domains similar to the GTF enzymes and GbpC is cell wall associated and is critical for sucrose-dependent cell-cell aggregation and biofilm formation. Although glucan synthesis appears to be important for binding to DM as Applicant observed enhanced binding when *S. mutans* was grown in the presence of sucrose, Applicant does not know if non-GTF GBPs play a role in DM adherence. Since the structure of the DM closely mimics that of the glucan produced by *S. mutans*, it is plausible that some or all of the non-GTF GBPs play a role in binding to DM, which could explain why Applicant sees considerably less attachment to DM with GS-5 WT and the GS-5 gtfBCD deletion mutant strains which have natural deficiencies in gbpC. It could also explain why the *S. mutans* strain BM71 displayed enhanced binding to DM even in the absence of sucrose compared to the other WT strains tested in Applicant's assay. This is currently under investigation. Nonetheless, GTFs and GBPs are important virulence factors that aid in the colonization of *S. mutans* in the oral cavity, thus allowing us to take advantage of targeting them via DM for their subsequent removal and elimination. Indeed the enhancement of *S. mutans* binding to DM occurred in as little as 10 minutes after sucrose exposure, a realistic time frame in which *S. mutans* would be exposed within the oral cavity after sucrose consumption.

Visualization of *S. mutans* binding to DM was observed with scanning electron microscopy, confirming the results of Applicant's binding experiments, whereas little to no adherence was observed with *S. cristatus* and *E. coli* (FIGS. 5A-5J). Sucrose had a profound influence on the binding of *S. mutans* WT to DM, but no effect on *S. gordonii*, *S. cristatus*, *E. coli*, or *S. mutans* ΔgtfBCD demonstrating that glucan production and cell-cell aggregation greatly enhanced *S. mutans* WT adherence to DM. In addition, Applicant observed varying degrees of selective removal of other cariogenic and pathogenic bacteria over probiotic and commensal bacteria (Table 2). Oral streptococci produce GTFs and GBPs (Banas, J. A. et al. (2003) Critical Reviews in Oral Biology and Medicine: An Official Publication of the American Association of Oral Biologists 14:89-99) (although not to the same degree as *S. mutans* and *S. sobrinus* (Banas, J. A. et al. (2003) Critical Reviews in Oral Biology and Medicine: An Official Publication of the American Association of Oral Biologists 14:89-99)), thus it was not surprising that these bacteria also bound to the DM. Although many of these species are considered commensals, they also have the potential to become pathogenic. *S. sanguinis, S. oralis, S. mitis*, and *S. gordonii* all have been associated with infective endocarditis, caused by bacteria entering the blood stream after dental procedures and routine dental care such as brushing and flossing (Sonbol, H. et al. (2009) Oral Microbiol Immunol 24:177-182). *S. oralis* is now considered a significant pathogen and has been shown to cause bacteremia in immunocompromised individuals (Bochud, P. Y. et al. (1994) The American Journal of Medicine 97:256-264; Whalan, R. H. et al. (2006) Journal of Bacteriology 188:1031-1038). *S. gordonii* aids in the colonization of *Porphyromonas gingivalis*, a dental pathogen often associated with periodontitis, by allowing *P. gingivalis* to attach to its surface with specific receptors (Chung, W. O. et al. (2000) Infect Immun 68:6758-6762). While the aforementioned opportunistic pathogens adhered to DM, the more beneficial commensals like *S. salivarius, S. cristatus*, and *L. acidophilus*, which are considered probiotics (bacteria that provide healthful benefits including protection against potential pathogens), bound to DM least of all. In fact, *S. cristatus* has been shown to inhibit HIV replication (Wang, Z. et al. (2014) PloS One 9:e106078) and attenuates the virulence of *P. gingivalis* and *Fusobacterium nucleatum* (Xie, H. et al. (2012) Journal of Periodontal Research 47:578-583; Zhang, G. et al. (2011) Journal of Periodontal Research 46:558-567), another pathogen that plays a role in periodontal disease. Applicant's initial findings suggest DM are able to target not only *S. mutans*, but other caries-causing bacteria and opportunistic pathogens, while having less affinity for healthier commensals. Finally, while sucrose has been associated with a higher incidence of *S. mutans* within the oral cavity, its presence further selects *S. mutans* for removal using DM. Although the commensal oral streptococci do contain GTFs and GBPs they appear to bind DM with less affinity than the opportunistic and caries-causing species; Applicant suspects this is the result of the fact that the DM mimicry of glucans does not extend sufficiently to the glucan of each of the aforementioned streptococci or the expression of the GTFs were not optimal during Applicant's assays. In contrast, Applicant predicted that the *Lactobacillus* strain tested in Applicant's study would not bind to DM since it does not possess GTFs or GBPs, although it does produce fructosyltransferases (FTFs), enzymes that utilize sucrose to synthesize fructan (Tieking, M. et al. (2005) Journal of Applied Microbiology 99:692-702). Fructan is composed of fructose molecules joined by β 2-1 or β 2-6 linkages (Velazquez-Hernandez, M. L. et al. (2009) Journal of Applied Microbiology 106:1763-1778) that differs from glucan produced by the oral Streptococci which is composed of glucose molecules linked by α 1, 3, α 1, 4 and/or α 1, 6 glycosidic bonds (Bowen, W. H. et al. (2011) Caries Research 45:69-86). Based on Applicant's results it does not appear that FTFs bind DM or it is possible that the FTFs produced by the Lactobacilli were not expressed during Applicant's assay. *E. coli* does not possess GTFs or GBPs and as expected this organism did not bind to DM.

A major advantage of using DM is the ability of loading cargo within the microsphere lumen. DM is supplied as a dry powder and when hydrated is insoluble in most common aqueous solutions. Using this to Applicant's advantage, Applicant filled the microspheres with hydrogen peroxide and chlorhexidine, two common antimicrobial agents found in a variety of oral health care products. The relatively small cargo volume within the spheres allows for more concentrated delivery of the cargo without flooding the entire oral cavity. In addition, the toxic cargo allows for targeted removal and elimination of bacteria that adhere to the microspheres. As a proof of principle, this study demonstrated that bactericidal agent-loaded DM preferentially bound and eliminated *S. mutans*, whereas *E. coli* cells that do not adhere to DM were protected from the toxic cargo within the lumen. Although the toxic cargo present in microspheres in Applicant's assay provided a protective effect compared to having the same volume of antimicrobials present without microspheres, Applicant did observe a detectable killing of *E. coli*. One reason for this result is the diffusion of cargo from the microspheres. It is highly likely that some of the toxic cargo readily diffused out from the DM lumen albeit at a lower final concentration as the contents are diluted by the volume of the entire oral cavity. Future experiments with diffusion-controlled release of antimicrobial compounds will likely further reduce this bystander effect. This is currently being investigated in Applicant's laboratory.

Of the over 700 bacterial species in the oral cavity, a large portion are naturally occurring non-pathogenic commensals that play important roles in human health (Aas, J. A. et al. (2005) J. Clin. Microbiol 43:5721-5732; Filoche, S. et al. (2010) Journal of Dental Research 89:8-18). These bacteria can help outcompete and prevent colonization by pathogens and stimulate immune functions. As with any part of the human body, disruption of the natural microbiota can lead to diseases which in the oral cavity includes dental caries and periodontal disease. Maintenance of healthy commensal microbiota in the mouth is also believed to discourage other pathogenic bacteria and yeast from transiently colonizing, where they can then disseminate to other areas of the body and cause disease. In fact, *S. mutans* has been shown to be associated with infective endocarditis (Nomura, R. et al. (2006) Journal of Medical Microbiology 55:1135-1140; Gauduchon, V. et al. (2001) Clinical Microbiology and Infection: The Official Publication of the European Society of Clinical Microbiology and Infectious Diseases 7:36-37; Lockwood, W. R. et al. (1974) Annals of Internal Medicine 80:369-370; McGhie, D. et al. (1977) British Heart Journal 39:456-458; Moore, J. et al. (1977) Irish Journal of Medical Science 146:144-145; Nakano, K. et al. (2009) Future Microbiology 4:891-902; Robbins, N. et al. (1977) Archives of Internal Medicine 137:1171-1174; Smith, J. P. et al. (1977) The American Journal of Medical Technology 43:429-432; Ullman, R. F. et al. (1988) Heart & Lung: The Journal of Critical Care 17:209-212; Vose, J. M. et al. (1987) The American Journal of Medicine 82:630-632), thus there is an increased need to develop methods to treat the bacteria that are causing the disease without eliminating the beneficial bacteria. A recent study by Horev et al., demonstrated that farnesol-containing nanoparticles allowed concentrated delivery of farnesol in a pH-dependent manner to *S. mutans* biofilms (Horev, B. et al. (2015) ACS Nano 9:2390-2404). In addition, a recent study by Haeseeb et al., used nanoparticles filled with chlorhexidine for drug delivery within the oral cavity for use in root canal procedures (Haseeb, R. et al. (2016) Materials 9:452). Although these new studies provide an innovative method of treating oral biofilms, it would most likely also affect the normal healthy microbiota. Here Applicant proposes a new novel strategy that could potentially be used in the treatment of dental caries where toxic cargo-loaded (e.g., hydrogen peroxide and chlorhexidine) microspheres target and eliminate caries-causing bacteria while leaving the healthy microbiota minimally disturbed. Furthermore, it has been shown that the oral commensals S. gordonii and S. sanguinis harbor resistance to hydrogen peroxide (Xu, Y. et al. (2014) Microbiology 160:2627-2638), thus allowing the potential targeted elimination of caries-causing S. mutans via hydrogen peroxide-loaded DM. Although this study was focused on S. mutans, a number of oral streptococci that make up the initial colonizers within the oral cavity also adhered to DM (Table 2). Not only are these bacterial species known to be opportunistic pathogens and are found within the cariogenic community, they possess GBPs which bind glucans produced by S. mutans thereby promoting the binding and colonization of S. mutans itself (Lynch, D. J. et al. (2013) Oral Health and Dental Management 12:191-199). Therefore the ability of these organisms to be removed and eliminated from the oral cavity could have potential health benefits. Although beyond the scope of this study, Applicant is interested in how the microbiome is effected by DM treatment, as this would provide insight on the selectivity of DM. This study is proof of concept to introduce the potential utilization of DM as a means to selectively remove caries-causing pathogens as current strategies to treat dental caries are broad spectrum and effect the entire microbial population.

Figure 9:
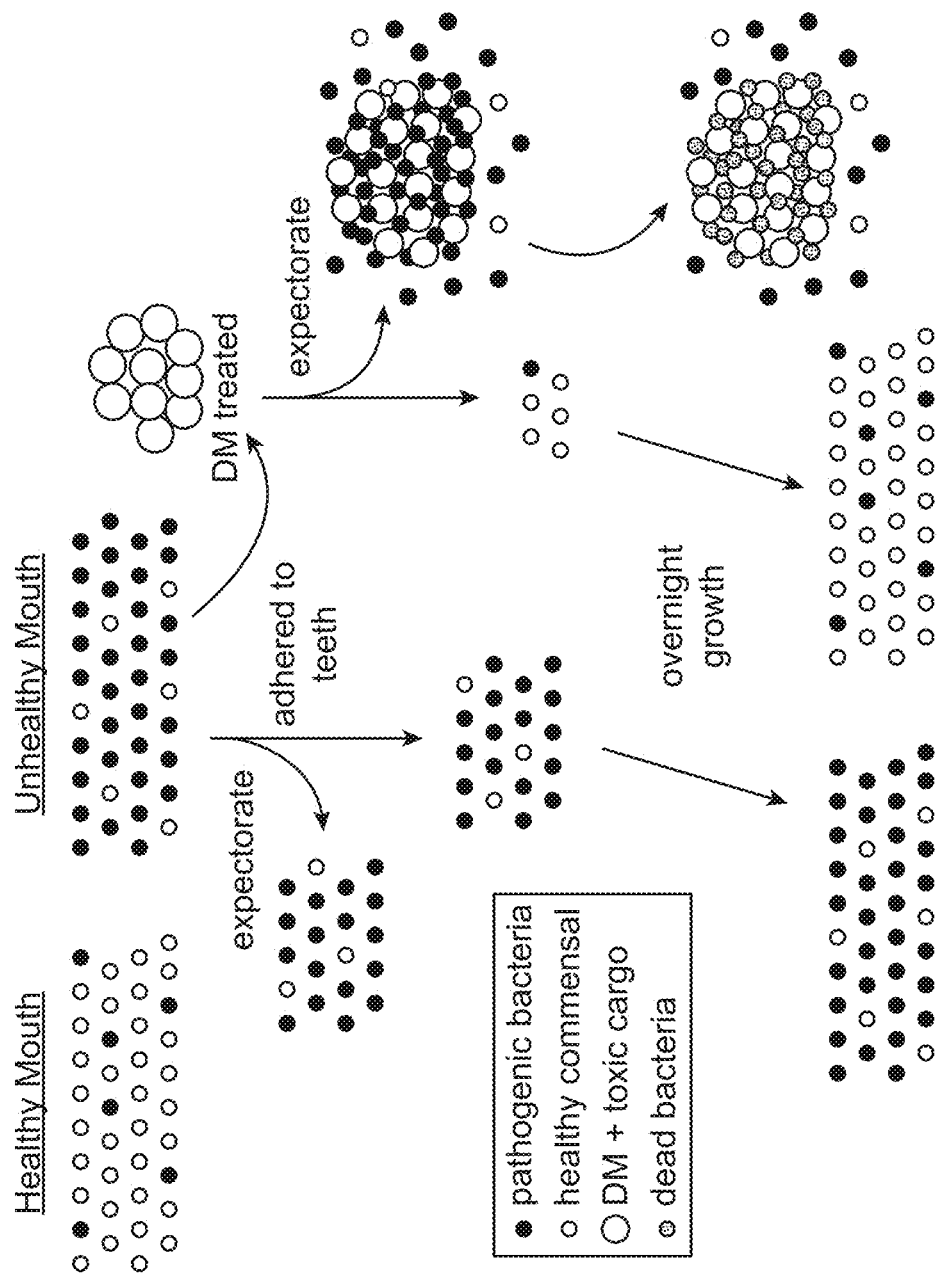
FIG. 9 shows potential outcomes of DM treatment. A simplified illustration shows a healthy mouth whose microbiome contains more healthy commensal bacteria versus an unhealthy mouth comprising mostly pathogenic/cariogenic bacteria. After expectoration or mouthwash exposure (left), an equal proportion of healthy and pathogenic bacteria exit the mouth, with the remaining bacteria in the same proportion able to adhere to the tooth surface; after overnight growth the pathogenic bacteria retain their predominant status within the oral cavity. In contrast, DM treatment (right) containing antimicrobial cargo causes pathogenic planktonic and biofilm bacteria to preferentially adhere to the DM causing selective removal and killing of these unhealthy bound bacteria, leaving the healthy commensals minimally disturbed initiating a shift from a more pathogenic to healthy state. Note figure is not drawn to scale.

Much effort and capital have been exhausted in finding efficient and affordable methodologies to maintain oral health by elimination of cariogenic pathogens. All current methods rely on either general reduction in the oral microbiota or in the protection of the tooth surface itself. As an alternative to these methods, Applicant has identified a well-characterized non-toxic FDA approved resin that is already used in various formulations in humans to treat wound infections and fecal incontinence (known as Debrisan and Solesta® respectively) (Hoy, S. M. (2012) Drugs 72:1671-1678; Parulkar, B. et al. (1985) Journal of Postgraduate Medicine 31:28). DM is insoluble, which is advantageous since it will remain out of solution and thus could have prolonged action when used in current oral health care delivery systems, e.g., toothpaste or mouthwash. DM resin does not have antimicrobial properties but rather appears to physically bind to S. mutans with high specificity. With further investigation DM could be used to develop a therapeutic oral health product to specifically remove or reduce plaque-causing bacteria from the oral cavity without disturbing the 'good' commensal bacterial population a possible means to drive a dysbiotic microbial population back to a healthy state, as illustrated in FIG. 9 where a healthy mouth contains predominantly healthy commensals and less pathogenic bacteria compared to an unhealthy mouth where the microbiome consists of predominantly pathogenic caries-causing bacteria (i.e., S. mutans) with fewer healthy beneficial commensals. Following expectoration or antimicrobial treatment, an equal amount of pathogenic and commensal bacteria are killed or removed, allowing the disproportioned ratio with more pathogenic bacteria to maintain their dominant status after overnight growth. In contrast, treatment of an unhealthy mouth with DM containing toxic cargo will specifically bind to the caries-causing pathogens, killing those that have bound leaving the healthy commensal bacterial negligibly disturbed. After repeated doses, the DM treatments will initiate a shift from a more pathogenic to healthy state.

TABLE 1

List of bacteria tested for binding to DM.

| Bacterial Strains | Relevant characteristics | Source or reference |
|---|---|---|
| *Streptococcus mutans* | | |
| UA159 | Wild type, serotype c | Lin Tao, University of Illinois at Chicago |
| UA159 (MW30) | Erythromycin$^R$ | (Desai, K. et al. (2012) Journal of Bacteriology 194: 3774-3780) |
| UA140 | Wild type, serotype c | (Qi, F. et al. (2001) Applied and Environmental Microbiology 67: 15-21) |
| GS-5 | Wild type, serotype c, naturally gbpC$^-$, pac$^-$ | (Senadheera, M. D. et al. (2007) Journal of bacteriology 189: 1451-1458) |
| BM71 | Wild type, serotype c | (Cvitkovitch, D. G. et al. (1995) Journal of Bacteriology 177: 2251-2258) |
| NG8 | Wild type, serotype c | (Cvitkovitch, D. G. et al. (2000) FEMS Microbiology Letters 182: 149-154) |
| UA159:gtfBCD | gtfBCD-deficient; Em$^R$, Tet$^R$ | Herein |
| GS-5:gtfBCD | gtfBCD-deficient; Em$^R$, Tet$^R$ | (Hanada, N. et al. (1989) Infect Immun 57: 2079-2085) |
| *Escherichia coli* | | |
| N99 | Lab strain used as a transformation host | (Rosenberg, M. et al. (1983) Methods in Enzymology 101: 123-138) |
| Other *Streptococcus* species | | |
| *Streptococcus oralis* | causes endocarditis | ATCC 10557 |
| *Streptococcus sanguinis* | primary colonizer, can cause sub-acute endocarditis | ATCC 10556 |

TABLE 1-continued

List of bacteria tested for binding to DM.

| Bacterial Strains | Relevant characteristics | Source or reference |
|---|---|---|
| Streptococcus sobrinus | causes dental root caries | OMZ 176 |
| Streptococcus cristatus | non-invasive oral bacteria | ATCC 49999 |
| Streptococcus mitis | very mildly opportunistic | ATCC 33399 |
| Streptococcus gordonii | primary colonizer, causative agent of infective endocarditis | Challis CH1 |
| Streptococcus salivarius | probiotic, typical live culture found in yogurt | ATCC 9222 |
| Streptococcus thermophilus | probiotic, typical live culture found in yogurt | LMD-9; ATCC BAA-491 |
| Lactobacillus species | | |
| Lactobacillus acidophilus | probiotic, typical live culture found in yogurt | ATCC 314 |

TABLE 2

Percent cells of various species that adhered to DM in Applicant's assay[a].

| Bacterial Species | Media[b] | Media + 3% sucrose[c] |
|---|---|---|
| Streptococcus sobrinus | 74.3%*** ± 13.0% | 89.7%[ns] ± 2.1% |
| Streptococcus sanguinis | 63.7%** ± 16.2% | 54.3%[ns] ± 18.6% |
| Streptococcus mitis | 61.7%**** ± 3.1% | 60.0%[ns] ± 12.5% |
| Streptococcus oralis | 60.7%*** ± 7.8% | 58.3%[ns] ± 8.4% |
| Streptococcus gordonii | 55.7%*** ± 19.6% | 49.7%[ns] ± 15.4% |
| Streptococcus thermophilus | 31.0%** ± 4.0% | 16.3%[ns] ± 10.4% |
| Streptococcus salivarius | 25.3%[ns] ± 17.8% | 32.0%[ns] ± 10.8% |
| Streptococcus cristatus | 10.0%[ns] ± 7.0% | 7.3%[ns] ± 8.4% |
| Lactobacillus acidophilus | 10.3%[ns] ± 9.0% | 13.3%[ns] ± 9.0% |
| Escherichia coli | 9.0%[ns] ± 7.8% | <1%[ns] |

[a]Cells were grown to early log phase and incubated for 5 min. with 12.5 mg of G-25 superfine DM.
[b]Statistics indicate values of cells adhered in the presence of THB and DM vs. THB without DM.
[c]Statistics indicate values of cells adhered in the presence of sucrose and DM vs. THB and DM.
**$P < 0.005$,
***$P < 0.001$,
****$P < 0.0001$,
ns = not significant The foregoing description of exemplary embodiments of the invention have been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents

What is claimed is:

1. A microsphere 20 μm to 50 μm in diameter when dry, comprising an antimicrobial agent encapsulated within an insoluble cross-linked dextran polymer, wherein the antimicrobial agent comprises one or more from the group hydrogen peroxide, chlorhexidline, penicillin, streptomycin, erythromycin, xylitol, fluride, triclosan, alcohol and cetylpridinium chloride.

2. The microsphere of claim 1 and a carrier and optionally one or more of a flavoring agent, a color, a preservative, a buffer, and a stabilizer.

3. The microsphere of claim 1, wherein the surface area of the microsphere is from about $6 \times 10^2$ μm$^2$ to about $6 \times 10^8$ μm$^2$ per mg of cross-linked dextran polymer.

4. The microsphere of claim 1, further comprising a carrier, wherein the concentration of the antimicrobial agent is from about 1 mg/μl to about 3 mg/μl of a carrier in the microsphere.

5. The microsphere of claim 1, wherein the dextran is cross-linked with epichlorohydrin.

6. A composition comprising a plurality of the microspheres of claim 1.

7. A composition comprising a plurality of the microspheres of claim 6.

8. The composition of claim 6 or 7, wherein the plurality of the microspheres have the same or different diameter and/or the same or different antimicrobial agent.

9. The composition of claim 6 or 7, wherein the composition is formulated as a solid, a semi-solid, or a liquid, and optionally as a gum, a gel, a toothpaste, a mouthwash, a lozenge, or a tablet, a chewable tablet, a suspension, a dissolvable lozenge, or a fluoride rinse.

10. A method for selectively inhibiting the growth of, and/or selectively removing carie-causing organisms from the oral cavity in a subject, comprising administering to the oral cavity of the subject an effective amount of the composition of claim 9, thereby inhibiting the growth of, and/or selectively removing carie-causing organisms from the oral cavity.

11. A method for treating and/or preventing infective endocarditis (IE) in a subject, comprising administering to the oral cavity of the subject in need thereof, an effective amount of the formulation of claim 8, thereby treating and/or preventing infective endocarditis.

12. A kit comprising a plurality of the microsphere of claim 1, and instructions for use.

13. The composition of claim 6 or 7, further comprising sucrose.

* * * * *

UNITED STATES PATENT AND TRADEMARK OFFICE
CERTIFICATE OF CORRECTION

| | |
|---|---|
| PATENT NO. | : 11,484,479 B2 |
| APPLICATION NO. | : 16/437921 |
| DATED | : November 1, 2022 |
| INVENTOR(S) | : Steven David Goodman and Lauren Mashburn Warren |

It is certified that error appears in the above-identified patent and that said Letters Patent is hereby corrected as shown below:

In the Claims

Column 30, Line 19 Claim 1 – "chlorhexidline" should be replaced with "chlorhexidine".

Column 30, Line 20 Claim 1 – "fluride" should be replaced with "fluoride".

Column 30, Line 26 Claim 3 – "$6 \times 10^2 \ \mu m^2$" should be replaced with "$6 \times 10^7 \ \mu m^2$".

Signed and Sealed this
Seventh Day of March, 2023

Katherine Kelly Vidal
*Director of the United States Patent and Trademark Office*